(12) United States Patent
Brailovski et al.

(10) Patent No.: US 8,308,761 B2
(45) Date of Patent: Nov. 13, 2012

(54) BINDING COMPONENT

(75) Inventors: Vladimir Brailovski, Montreal (CA);
Raymond Cartier, Montreal (CA);
Patrick Terriault, Verdun (CA);
Yannick Baril, Montreal (CA)

(73) Assignee: Ecole de Technologie Superieure, Montreal (CA)

( * ) Notice: Subject to any disclaimer, the term of this patent is extended or adjusted under 35 U.S.C. 154(b) by 1502 days.

(21) Appl. No.: 11/791,016

(22) PCT Filed: Dec. 6, 2005

(86) PCT No.: PCT/CA2005/001859
§ 371 (c)(1),
(2), (4) Date: May 18, 2007

(87) PCT Pub. No.: WO2006/060911
PCT Pub. Date: Jun. 15, 2006

(65) Prior Publication Data
US 2008/0119892 A1    May 22, 2008

Related U.S. Application Data

(60) Provisional application No. 60/633,512, filed on Dec. 6, 2004.

(51) Int. Cl.
*A61B 17/03* (2006.01)
*A61B 17/82* (2006.01)
(52) U.S. Cl. ............... 606/215; 606/151; 606/228
(58) Field of Classification Search ............. 606/74, 606/151–153, 213–217, 228–231
See application file for complete search history.

(56) References Cited

U.S. PATENT DOCUMENTS

| | | | |
|---|---|---|---|
| 4,730,615 A | 3/1988 | Sutherland et al. | |
| 4,813,416 A | 3/1989 | Pollak et al. | |
| 5,318,575 A | 6/1994 | Chesterfield et al. | |
| 5,330,489 A | 7/1994 | Green et al. | |
| 5,356,412 A | 10/1994 | Golds et al. | |
| 5,356,417 A | 10/1994 | Golds | |
| 5,766,218 A * | 6/1998 | Arnott | 606/151 |
| 6,030,410 A * | 2/2000 | Zurbrugg | 606/219 |
| 7,648,504 B2 * | 1/2010 | Heino et al. | 606/74 |
| 2004/0015187 A1 | 1/2004 | Lendlein et al. | |

OTHER PUBLICATIONS

Cheng et al., "Biomechanical Study of Sternal Closure Techniques", Ann Thorac Surg 1993; 55:737-740.*
Heart disease and stroke statistics—2005 Update. (2005). Dallas: American Heart Association.
Milton, H. (1987). Mediastinal surgery. Lancet, 1, 872-875.
Robicsek, F., Daugherty, H. K., & Cook, J. W. (1977). The prevention and treatment . . . The Journal of Thoracic and Cardiovascular Surgery, 73(2), 267-268.
Casha, A. R., Gauci, M., Yang, L., Saleh, M., Kay, P. H., & Cooper, G. J. (2001). Fatigue testing median . . . European Journal of Cardiothoracic Surgery, 19(3), 249-253.
Soroff, H. S., Hartman, A. R., Pak, E., Sasvary, D. H., & Pollak, S. B. (1996). Improved sternal closure using steel . . . Annals of Thoracic Surgery, 61(4), 1172-1176.

(Continued)

*Primary Examiner* — Kathleen Sonnett

(57) ABSTRACT

A binding component for binding together a pair of biological tissues. The binding component includes an elongated body defining a body longitudinal axis, the body being made, at least in part, of a shape memory material. The body is configured and sized so as to be both substantially flexible and substantially compressible in a direction substantially perpendicular to said longitudinal axis.

6 Claims, 11 Drawing Sheets

OTHER PUBLICATIONS

Sargent, L. A., Seyfer, A. E., Hollinger, J., Hinson, R. M., & Graeber, G. M. (1991). The healing sternum: . . . The Annals of Thoracic Surgery, 52(3), 490-494.

Losanoff, J. E., Richman, B. W., & Jones, J. W. (2002). Disruption and infection of median sternotomy: . . . European Journal of Cardio-Thoracic Surgery, 21(5), 831-839.

Duerig, T., Pelton, A., & Stockel, D. (Mar. 1997). Superelasitic Nitinol for Medical Devices. Medical Plastics and Biomaterial Magazine MPV archive.Casha, A. R., Yang, L., K.

McGregor, W. E., Trumble, D. R., & Magovern, J. A. (1999). Mechanical analysis of midline . . . The Journal of Thoracic and Cardio. Surgery, 117(6), 1144-1145.

ANSYS. (2003). ANSYS (Version 8.0) [Finites elements]. Canonsburg, Pa, US.

Hale, J. E. et al (Oct. 21-23, 1999). A polyurethane foam model . . . Paper presented at the 23rd Annual Meeting of the American Society of Bio. University of Pittsburgh.

* cited by examiner

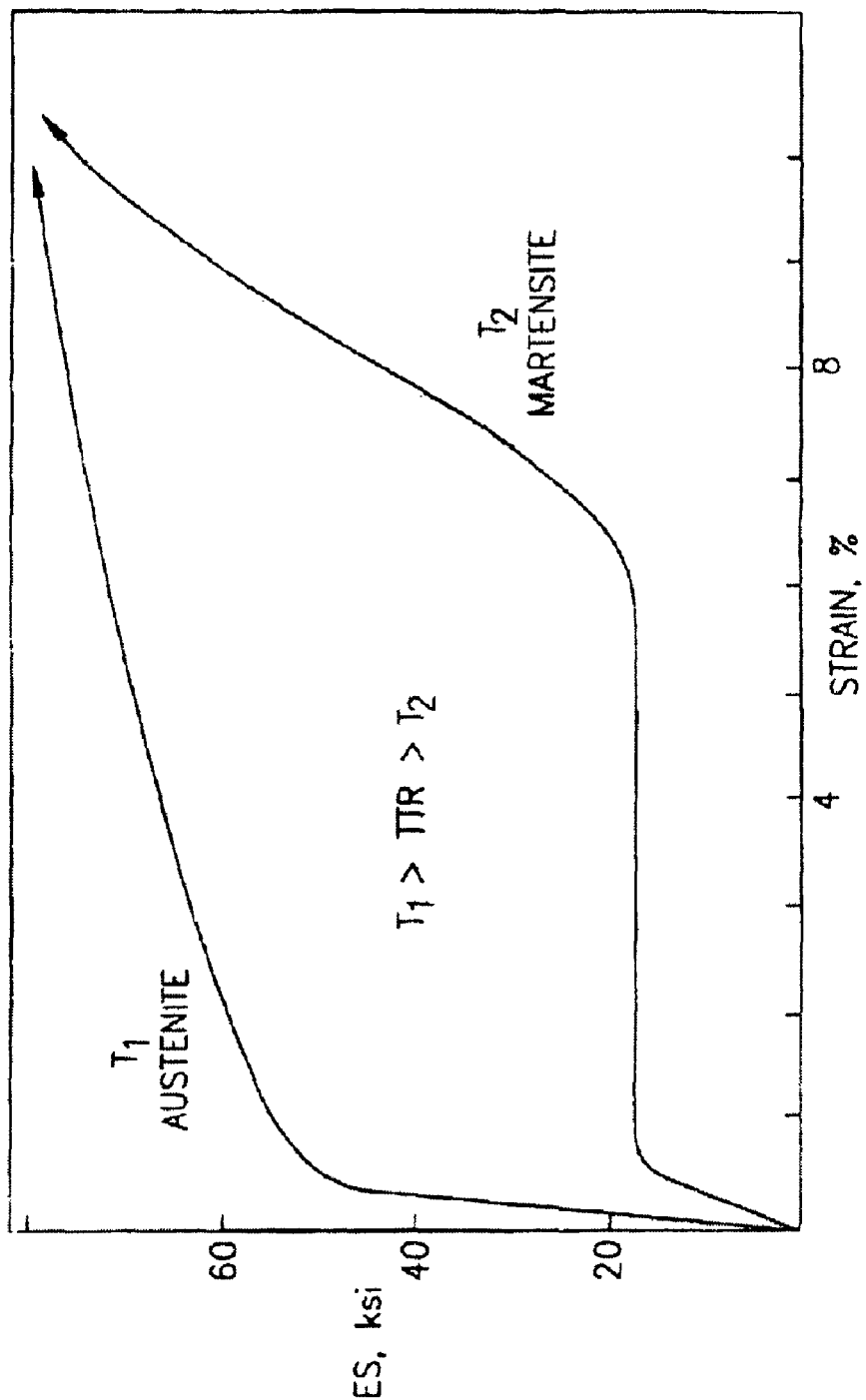

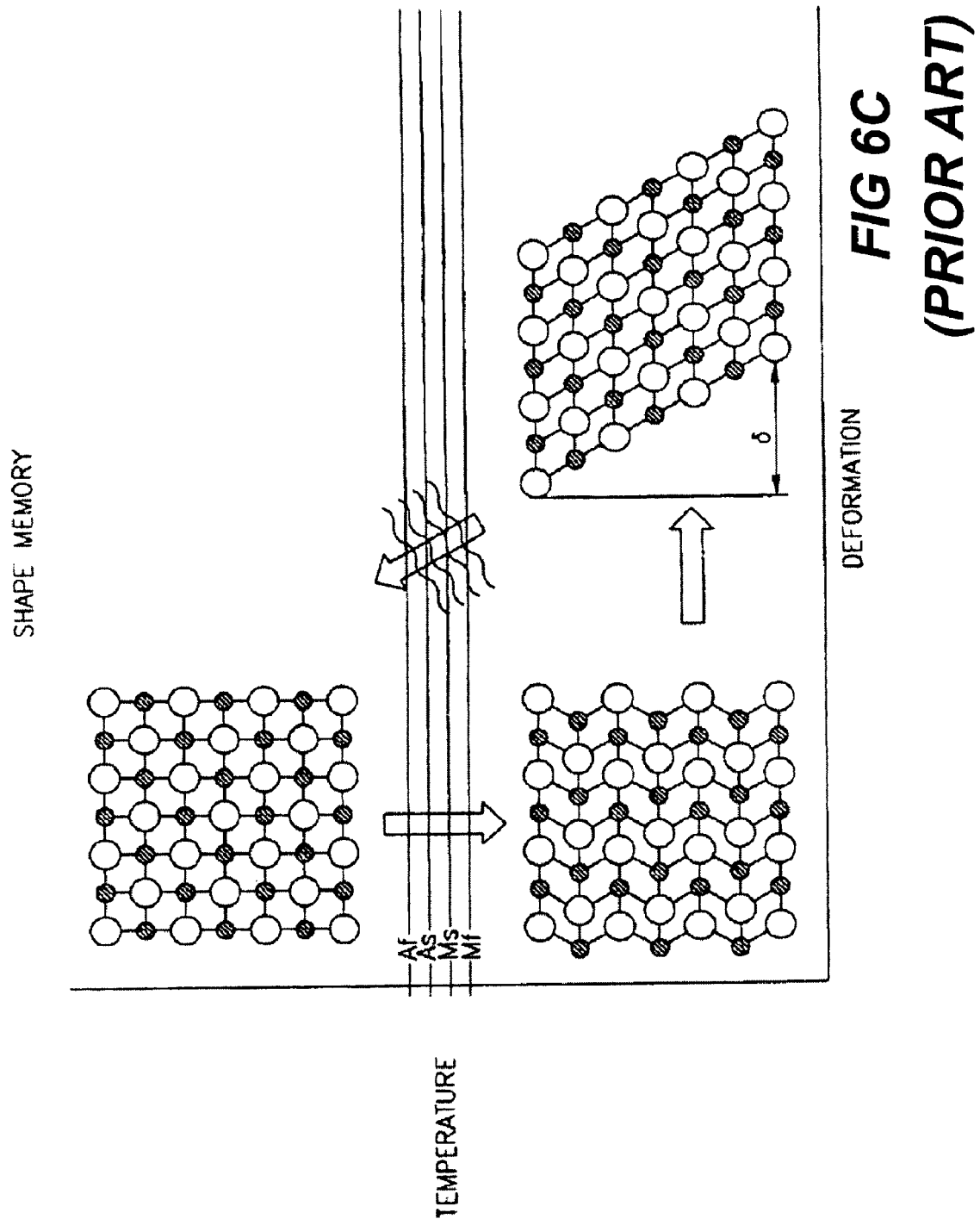

1) Frame
2) Sternum
3) Loading clamps
4) Tensile testing machine
5) Load cells
6) Sliders
7) Suture: t – transsternal; p – peristernal

BINDING COMPONENT

This is a National Stage Application of PCT/CA05/01859 under 35 USC §371(a), which claims priority of U.S. Provisional Patent Application Ser. No. 60/633,512 filed Dec. 6, 2004.

FIELD OF THE INVENTION

The present invention relates to the general field of binding components and is particularly concerned with a binding component suitable for binding together a pair of biological tissues.

BACKGROUND OF THE INVENTION

There exists a plurality of situations wherein it is desirable to bind together components having specific properties. For example, there are various circumstances in which separated tissue of a patient needs to be brought together so it can heal. Such tissue may include bone, muscle, fascia or the like that has been divided to gain access for example to the thoracic cavity, the mediastinum, the abdomen or the like.

Typically, most surgical procedures involving the heart or lungs are performed through a midline sternal incision, widely referred to as median sternotomy. After an incision is made through the skin, the sternum is cut longitudinally using specialized power saws. The cut extends the entire length of the sternum, from the sternal notch at the neck to the xyphoid. This midline cut allows the two halves of the sternum in the anterior portion of the ribcage to be spread several inches apart, giving the surgeon access to the thoracic cavity. During surgery, the two halves of the sternum are typically held apart by mechanical retractors.

Once the surgeon has finished the procedure regarding the chest cavity, the sternum needs to be closed or reapproximated. For proper healing to occur, the split sternum portions are preferably engaged in face-to-face relationship and compressed together while the sternum heals. The key to the healing process of the sternum is the proper stabilization and contact of the two severed sides together.

Heretofore, there have been many techniques used to bring the separate sides of the sternum together and maintain them in contact so the healing process can occur. In a vast majority of cases, surgeons use stainless steel wire closure devices. These closure devices are composed of a thin stainless steel wire with a diameter typically of about 0.5 to 1.5 mm coupled to a curved needle. The composite device is formed by inserting one end of the stainless steel wire into a cavity in the non-sharpened end of the curved needle which is then crimped tightly to secure the wire to the needle.

The needle is used to pass the wire through the sternum or around the sternal halves, between the ribs that connect to the sternal halves. After all the wire segments have been properly positioned, clamps positioned on each wire are sequentially picked up by the surgeon and the wires are twisted around each other.

The ends are then trimmed and the twisted junctures are twisted again to create an extra-snug closure that will ensure that the sternal bones are pressed tightly against each other to minimize bleeding and ensure proper fusing of the sternal halves into an intact sternum. Normally, the wire loops are left in place permanently. Unless problems arise which require a second surgical operation to remove the wires, they remain in place for the remainder of the patient's life, even after the sternal halves have fused together again.

Despite their widespread use, the stainless steel wires suffer from numerous drawbacks that can cause problems both to the surgeon and to the patient during the operation and to the patient after closure is completed. For example, the relatively stiff and unyielding characteristic of a stainless steel wire renders it unwieldy and sometimes difficult to manage on the operative field. Furthermore, after each wire is in place, the segment that sits below the sternal halves may press down on body tissues such as a coronary artery by-pass graft or the heart itself while the other wires are being placed. Injury to these soft tissues can hence occur from these stiff wire segments during the normal course of sternal closure.

Also, during either preparation or application, the free end of a sternal wire can stab a surgeon, scrub nurse, or assistant. This substantial problem is compounded by the fact that the wire is typically cut using a wire cutter with relatively blunt blades, which generates a chiselled point that is typically quite sharp. To reduce the risks of stab wounds to the surgeons and their assistants, clamps are now typically used to secure the free ends of any wire in a patient's chest. However, such clamps are also plagued with various drawbacks including cluttering of the operating field and being tedious and time consuming to work with and around.

Furthermore, the stainless steel sternal wires can disrupt the entire image generated in a computerized axial tomography or magnetic resonance imaging scan of the chest for the remainder of the patient's life.

Still furthermore, tightening by twisting wires together with a pair of pliers is an inexact method. The surgeon has to develop a sensitive field for how much torque needs to be applied to properly tighten the wire without breaking it. Consequently, some suture wires break during installation. A wire break requires the surgeon to undo all finished sutures and start the process all over again.

Sternal wires occasionally also break after the surgery. Such breakage can be secondary to the thinning and deformation of the steel strand by the excessive force or stresses that are sometimes applied to the loop during routine closure. For fear of breaking a wire, a surgeon may tend to under-torque the suture, resulting in less than optimal closure pressure on the sternal knit line. This, in turn, can lead to dehiscence problems.

A particularly major problem associated with steel wire sutures is that post-operative stress on the closure loops may cause the thin wires to cut into and through the bone of the sternum. Indeed, since wires inherently define a relatively small contact surface, anatomical structures may experience excessive localized pressure resulting in damage. For example, bone may fracture or experience necrosis, cartilage may tear, etc.

Typically, most of the tension resulting from the twisting procedure on the wire is applied at the anterior surface of the sternum. Routine postoperative care of cardiothoracic patients requires aggressive pulmonary rehabilitation including early ambulation. The coughing, deep breathing and movement required to attain these goals imposes substantial stresses on the sternal closure. These substantial stresses may, in turn, cause the wire loops to cut the bone in an inward direction at the posterior side of the sternum. Elderly patients or patients who have thin or osteoporotic bones are particularly susceptible to this complication.

The result is further loosening of the sternal closure which can lead to painful instability of the two sternal halves with respiratory compromise and ultimately sternal dehiscence. Instability of the sternal closure can also result in internal bleeding. This, in turn, can increase the risks of infection and/or result in macerative damage to the cartilage and associated muscle tissue with a consequent increase in post-operative discomfort and in the time required for healing. Also, if a second operation for sternal rewiring is required, it is made even more difficult by the fact that the sternal halves are often sliced into pieces by the stainless steel wires.

The problem of sternal dehiscence after closure using suture loops is known, and, various solutions have been proposed. Among these are reinforcement of the sternum by implantation of longitudinally extending wires or weaving reinforcement wires around the ribs adjacent to the sternum and then applying sutures peristernally to join the sternal halves. However, these proposed solutions tend to result in increased damage to blood vessels or other soft tissue, and also may substantially increase the time required for closing the chest. Also, if infection occurs necessitating removal of the sutures, it can be very difficult to remove the reinforcing wires.

In an effort to circumvent some of the disadvantages associated with steel wires and, more particularly, to reduce the risk of having the closure structures cut into and through the bone of the sternum, substantially flat bands have been proposed. For example, U.S. Pat. No. 4,730,615 issued to Sutherland and Vasconcellos in 1988 describes a flat band made of metal and coated with plastic, which slides through a fastener device which was referred to in the patent as a "buckle". The band contains protruding serrations which interact in a ratcheting manner with an angled tang in the buckle. This allows the band to be pulled tight while the tang slides across the raised serrations. Subsequently, if tension exerted attempts to expand or open the loop, the angled tang presses against the shoulder of a serration, thereby preventing the band from moving in the opposite direction.

A somewhat similar structure is disclosed in U.S. Pat. No. 4,813,416 issued to Pollak and Blasnik in 1989. This patent discloses a flat stainless steel band with notches rather than serrations. The notches interact with bumps in a buckle device, to hold the band securely after the band has been pulled tight.

U.S. Pat. No. 5,356,412 issued Oct. 18, 1994 to Golds and Muth discloses a strap assembly to be looped about split portions of human tissue including a flexible elongated member and a buckle member. The buckle member includes a frame member and a clamp member rotatably mounted within the frame member for movement from a non-strap securing position to a strap securing position. The clamp member rotates to the strap securing position in response to tensional forces exerted on the strap during tensioning thereof about the tissue portions.

These band-like devices provide an increased contact surface with the sternum as compared to the steel wires, and, hence, theoretically reduce the risk of cutting into and through the bone of the sternum. However, they nevertheless suffer from various limitations which limit their utility.

For example, being substantially flat and made of relatively stiff and unyielding material, they are typically unable to fittingly contact the geometry of the sternum. Also, their geometry is such that they cannot penetrate easily through the bone and, hence, can only be positioned peristernally between the ribs. Being relatively large, they typically displace the peristernal structures such as muscles.

Furthermore, because of their flat configuration, their bending moment of inertia is polarized in a predetermined direction. Consequently, they are considered unergonomical. Typically, they are even more unwieldy and difficult to manage on the operative field than steel wires.

Still furthermore, the substantially flat shape of these bands results in relatively sharp side edges. Such sharp side edges can slice into the surrounding tissues or bones like a blade when they are pulled through behind the needle. This, in turn, may cause internal haemorrhaging and associated problems. The sharp side edges, if unprotected, also have considerable potential to slide into the fingers of the operating surgeon or assistants. Furthermore, they are capable of inflicting injury to the soft tissues below the sternum during closure.

Another type of closure system attempting to circumvent problems associated with steel wires and disclosed in the prior art uses clamps. Examples of such closure systems are disclosed, for example, in U.S. Pat. No. 4,201,215 to Crossett et al and in U.S. Pat. No. 6,217,580 issued Apr. 17, 2001 to L. Scott Levin.

The sternal clamping device disclosed in the latter patent includes a pair of opposed generally J-shaped clamp members which are laterally adjustable relative to one another and can be rigidly joined via a set of machine screws. The threaded coupling of these set screws rigidly unites the clamp members one to another without lateral shifting occurring over time.

This type of system is relatively rigid and reliable. However, the components thereof are relatively large and may cause serious pain or other ailments to the patient. It is hence typically reserved to patients having an increased risk of sternal rupture or with important risk factors for infection.

In an effort to circumvent the problem of cutting into and through bone of the sternum associated with conventional steel wires, attempts have also been made to offer radially compressible sutures offering an increased contact surface area as evidenced by U.S. Pat. No. 5,423,821 issued Jun. 13, 1995 to Michael K. Pasque, the entire contents of which are incorporated expressly hereinto by reference.

According to the Pasque patent, a strand of thin flexible suture material is used which is compressible in its radial dimension but remains strong and relatively inelastic in its longitudinal dimension. The compressibility in the radial direction results either from the hollow tubular shape or the compressible nature of the materials used. The longitudinal strength may be maintained by nylon fibres or other materials for reinforcement.

The soft suture material helps cushion, distribute and minimize the stresses and damage inflicted on the sternum or ribs post-operatively. Furthermore, when not compressed, the strand has a diameter slightly larger than the diameter of the needle. Hence, after insertion, the expandable suture material provides gentle pressure against the surrounding tissue to minimize bleeding in the needle track.

A common problem to all of the hereinabove mentioned bone binding structures is that they can only be used towards fixation of the sternal halves, i.e. for immobilizing the sternal halves in close proximity to each other. However, for osteogenesis and solid union of the sternal halves to occur, compression of the sternal halves at the break boundary must be maintained during the healing process.

Fixation is a static process whereas compression is a dynamic one. Compression is dynamic because it must be maintained during dimensional redefinition occurring at the break boundary during healing. With the hereinabove mentioned prior art structures, compression across the break boundary typically decreases substantially during the healing process.

Indeed, the width of the sternum tends to decrease due to the nature of the healing process. The above-mentioned structures cannot respond to this dimensional change and, consequently, cannot maintain compression across the facing boundaries of the divided sternum during the healing process. Thus, applied pressure decreases with time.

As stated above, not only do the large initial compression forces generated with the hereinabove mentioned devices diminish in the initial phase of bone healing, but such large forces, in themselves, are detrimental relative to the concentrated forces experienced proximal to the wires. Although the hereinabove mentioned structures provide some stability, they are deficient as a means to establish a known initial force and they never reconcile the need for continuous compressive force. Furthermore, physiological activities such as coughing contribute to the degeneration not only of the sternum but also potentially of the devices themselves.

The need for providing a binding structure capable of inducing a compression at the break boundary of the divided sternum has been recognized and addressed in U.S. Pat. No. 5,766,218 issued Jun. 16, 1998 to Richard J. Arnott. The disclosed binding device includes a strap adapted to form a loop about injured tissue and a tension member attached to the strap. The tension member is adapted to maintain a predetermined stress level in the loop which compresses the edges of the tissue together to foster healing. The tension member is preferably a shape memory effect alloy, such as Nitinol, a nickel-titanium alloy. The binding device also includes a one-way locking mechanism which keeps the strap in the loop.

Also disclosed is a method of binding together injured tissue under a compressive force to promote healing. The method comprises the steps of drawing together in close proximity opposing edges of injured tissue by tightening a strap which forms loop about the injured tissue and tightening the strap so that a tension member within the strap exerts a substantially constant tension within the strap to maintain the tissue in close proximity.

The use of so-called shape memory materials such as shape memory alloys in the medical field has been disclosed in the prior art. These alloys have different phase structures, hence, different mechanical properties, at different temperatures. Information about shape memory alloys may be found, for example, on the web site www.nitinol.com, by Nitinol Devices & components, copyright 1998.

In brief, FIGS. 6A and 6B, together, schematically illustrate a typical temperature and stress hysteresis, typical elastic stresses, $\sigma_y$, in phase transitions, and typical stress-strain curves for a shape-memory alloy in the austenitic and martensitic phases. At low temperature, the alloy is martensitic, and is soft and plastic, having a low $\sigma_y$. At a high temperature, the alloy is austenitic and tough, having a high $\sigma_y$.

When a martensitic alloy is heated to a temperature $A_s$, the austenitic phase begins to form. Above a temperature $A_f$ the alloy is fully austenitic. Likewise, as an austenitic alloy is cooled to a temperature $M_s$, the martensitic phase begins to form. Below a temperature $M_f$ the alloy is fully martensitic.

The temperature-dependent phase structure gives rise to shape memory. At the fully austenitic phase, under proper heat treatment and working conditions, an SMA element can be given a physical shape and "pre-programmed" to memorize that shape and resume it, whenever in the austenitic phase. The "memorized" SMA element may then be cooled to a martensitic phase and plastically deformed in the martensitic phase. But when heated back to the austenitic phase it will resume its memorized shape. The transformation temperature range between the phases is noted as TTR.

The reason for the shape memory is found in the phase structure of the alloy. Most metals deform by atomic slip. Dislocations and atomic planes slide over one another and assume a new crystal position. In the new position, the crystal has no memory of its order prior to the deformation. With increased deformation, there is generally a work-hardening effect, in which the increased tangle of dislocations makes additional deformation more difficult.

This is the case even when the increased deformation is in the direction of restoring the crystal to its original shape. However, for shape memory alloys, both transitions between the austenitic and martensitic phases and deformation in the martensitic phase change lattice angles in the crystal, uniformly for the whole crystal. The original austenitic lattice structure is "remembered" and can be restored.

FIG. 6C schematically illustrates typical phase structures of a shape-memory alloy, as functions of temperature and deformation, as follows:
- in the austenitic phase, the crystal has a cubic structure, and the atoms in the lattice are arranged generally at right angles to each other;
- when the austenitic crystal is cooled to a martensitic phase, a twinned lattice structure is formed;
- when the twinned martensitic crystal is deformed by an amount no greater than δ, the twinned structure "stretches" so that the atoms in the lattice are arranged generally at oblique angles to each other, wherein the oblique angles are determined by the amount of deformation; and
- when the deformed martensitic crystal is heated, the crystal resumes its cubic structure, wherein, again, the atoms in the lattice are arranged generally at right angles to each other.

Another property that can be imparted to SMA elements, under proper heat treatment and working conditions, is so-called superelasticity, or Stress-Induced Martensite (SIM). With this property, a fully austenitic SMA element, at a temperature above $A_f$, will become martensitic and plastic under high stress, and deform under the stress. When the stress is removed, the SMA element will return to the austenitic phase and to its memorized shape in the austenitic phase.

Superelasticity is also referred to as rubber-band like property, because the SMA element behaves like a rubber band or a spring, deforming under stress and resuming its original shape when the stress is removed. However, this property is present only above the temperature $A_f$, and only when it is specifically imparted to an SMA element, by proper heat treatment and working conditions.

FIG. 6D schematically illustrates a typical cyclic transformation of a superelastic alloy, at a constant temperature above the temperature $A_f$. The transformation between the austenitic phase and a stress-induced martensitic phase is brought about by stress and is eliminated when the stress is removed.

Binding devices disclosed in the prior art using shape-memory alloys typically suffer from numerous drawbacks. For example, the structure disclosed in U.S. Pat. No. 5,766,218 is relatively complex to manufacture and, hence, potentially less reliable and more expensive. Furthermore, the use of a strap is associated with the hereinabove mentioned disadvantages inherent to its geometry.

Other medical binding devices using shape-memory alloys typically take the form of staples or clamps for bone fixation. They are easily inserted in a martensitic phase, then deformed to an open, straight-edge state, and they resume a closed, clamped state in the body, thus forming a closure on the fracture. However, again, they suffer from disadvantages inherently associated with their geometries.

Shape memory materials have also been used, inter alia, in the production of stents. As is well known, a stent is a generally tubular mesh-like device which is useful in the treatment of stenosis, strictures or aneurysms in body conduits defining lumens such as blood vessels. Shape memory material stents are designed so as to be expanded in the austenitic phase and compressed or partially expanded in the martensitic state. The shape memory alloy is typically chosen such that stent will be in the austenitic state at body temperature.

The role of the stent being to support, repair or otherwise enhance the performance of a body lumen, stents are specifically designed to provide a relatively high resistance to radial collapse. Hence, they actually teach away from the principles of the present invention as will be hereinafter disclosed.

Accordingly, against this background, there exists a need for an improved binding structure.

SUMMARY OF THE INVENTION

It is a general object of the present invention to provide such an improved binding structure. In accordance with the present invention, there is hence provided a binding component for binding together a pair of biological tissues, the binding component comprising an elongated body defining a body longitudinal axis; the body being made, at least in part, of a shape memory material; the body being configured and sized so as to be both substantially flexible and substantially compressible in a direction substantially perpendicular to the longitudinal axis.

Advantageously, the shape memory material demonstrates superelastic properties when subjected to environmental temperatures within the range of expected body temperatures.

Preferably, the body has a substantially uniform moment of inertia of bending in all directions. Typically, the body has a substantially hollow tubular configuration and is made of braided filaments of a shape memory material.

In accordance with the present invention, there is also provided a method for binding biological tissues together, the method including the steps of selecting a suitable binding component comprising an elongated body defining a body longitudinal axis; the body being made, at least in part, of a shape memory material; the body being configured and sized so as to be both substantially flexible and substantially compressible in a direction substantially perpendicular to the longitudinal axis; positioning the binding component in a binding configuration wherein the binding component biases the biological tissues in an opposite contacting relationship relative to each other, and inducing a pre-strain into at least part of the binding component. Preferably, the prestrain corresponds to an applied stress having a value of between $\sigma_{Ms}$ and $\sigma_{Mf}$.

In accordance with the present invention, there is further provided a method for manufacturing a binding component, the method comprising the steps of braiding filaments of shape-memory material into an elongated body defining a body longitudinal axis; the body being configured and sized so as to be both substantially flexible and substantially compressible in a direction substantially perpendicular to the longitudinal axis.

Conveniently, the method further comprises the step of treating the body so that the shape memory material demonstrates superelastic properties when subjected to temperatures substantially in the range of expected human body temperatures In accordance with the present invention, there is yet also provided a binding component for binding together a pair of biological tissues, the binding component comprising: an elongated body defining a body longitudinal axis; the body being made, at least in part, of a shape memory material; the body being provided with at least one therapeutic or prophylactic surgically useful substance.

The proposed binding structure is specifically design so as to synergistically combine the advantages associated with shape memory materials with advantages associated with its geometry.

More specifically, advantages of the present invention include that the proposed binding structure advantageously applies a substantially constant compressive force across tissue boundary while being able to accommodate some expansion.

The proposed binding structure protectively controls the maximum force that tissue in intimate contact therewith experiences. The proposed structure stretches at a known or programmable level and is then capable of returning to its pre-stretched lengths while generating a substantially constant force. The ability of the proposed structure to allow a relatively unlimited expansive force moderates local forces in the tissue around the binding structure, decreasing the likelihood of damaging or tearing the tissue.

Hence, the proposed binding structure is adapted to maintain cohesion between opposed tissue surfaces during the duration of osteogenesis even in situations wherein it is subjected to various stresses linked to post-operative events such coughing or the like.

The proposed system is also adapted to reduce the risks of disruption of the sternum by shearing imputable to a large exterior stress. In the event wherein sternal deterioration occurs, the proposed system is adapted to maintain a predetermined compressive load on the sternum in order to insure its cohesion.

Furthermore, the proposed binding structure is adapted to provide an increased contact surface when effectively providing a compressive force. Still furthermore, while providing an increased contact surface, the proposed binding structure is still deprived of relatively sharp edges that could potentially cause haemorrhaging or the like.

In short, the proposed binding structure is adapted to reduce the risks of the latter tearing through the sternal bone by both increasing the contact surface therewith and accommodating some degree of expansion. Furthermore, the proposed structure is adapted to maintain a compressive force at the interface of the two sternal halves despite the physiological remodelling during fusion thereof and even in situations wherein some degree of tearing as occurred in the bone.

Still furthermore, the proposed binding structure is designed so as to be ergonomically pliable, having a relatively low bending moment inertia, the latter being also substantially constant in all directions. This, in turn, facilitates ergonomical handling of the binding structure during the surgery and allows the binding structure to more fittingly contact the sternum.

Yet, still furthermore, the proposed binding structure is designed to show little if any tendency to kink or snarl. Also, the proposed structure is adapted to reduce the risks of injury to the surgeon or assistants thereof. Furthermore, the proposed structure is adapted to reduce the risks of compressing or otherwise damaging biological structures adjacent the sternum during installation thereof.

Also, the proposed binding structure is designed so be easily severed or otherwise rendered ineffective or removed in situations wherein, for example, the sternum needs to be re-opened. The proposed binding structure, for example, is adapted to be easily cut using a conventional surgical tool such as a surgical scissor or the like without requiring excessive force or manual dexterity.

Furthermore, the proposed binding structure is adapted to reduce the risks of creating imaging artefacts or otherwise interfering with medical imaging once in place.

Also, the proposed binding structure is designed so as to be manufacturable using conventional forms of manufacturing so as to provide a device that will be economically feasible.

In another broad aspect, the invention provides a method for binding biological tissues together, the biological tissues having a yield limit beyond which the biological tissues are irreversibly deformed. The method comprises:

selecting a suitable binding component comprising an elongated body defining a body longitudinal axis; the body being made, at least in part, of a shape memory material;

positioning the binding component in a binding configuration wherein the binding component biases said biological tissues in an opposite contacting relationship relative to each other;

wherein the binding component is at least in part prestrained with a prestrain causing the generation of a force within an interval of from about 80 percent to about 95 percent of the yield limit after said positioning of said binding component.

In yet another broad aspect, the invention provides a method for manufacturing a binding component.

In yet another broad aspect, the invention provides a binding component.

In some embodiments of the invention, the binding component has a binding component ultimate tensile strength within an interval of from about 200 N to about 300 N.

The composition, configuration and dimensions of the body may be selected such that an inflection point between an upper plateau of a force-displacement relationship of the binding component and a linear force-displacement relationship representing an elastic deformation of a stress-induced martensite phase in the binding component is substantially coincident with a force and a displacement representative of the prestrain in the body component and a difference in force between a lower plateau of the force-displacement relationship of said binding component and the upper plateau of the force-displacement relationship of said binding component is minimal.

BRIEF DESCRIPTION OF THE DRAWINGS

An embodiment of the present invention will now be disclosed, by way of example, in reference to the following drawings in which:

FIGS. 6A and 6B schematically illustrate a typical temperature histeresis and typical elastic stresses, $\sigma_y$, in phase transitions, for a typical shape memory material, in accordance with the prior art;

FIG. 6C schematically illustrates typical phase structures of a shape memory alloy, as functions of temperature and deformation, in accordance with the prior art;

DETAILED DESCRIPTION

Figure 1:
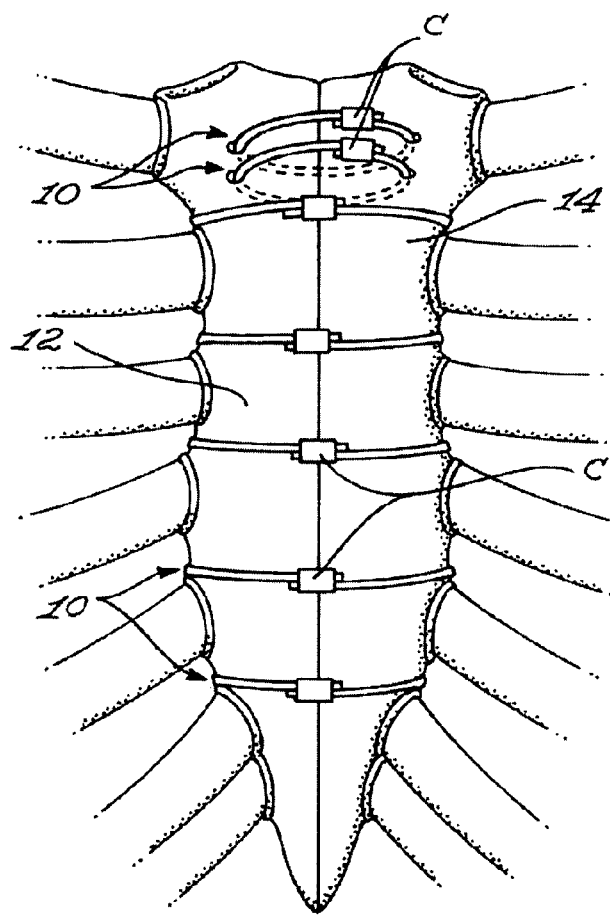
FIG. 1, in an elevational view, illustrates a pair of sternum halves being bound together using binding components in accordance with the present invention.

Referring to FIG. 1, there are shown binding components in accordance with an embodiment of the present invention, the binding components being generally indicated by the reference numeral 10. The binding components 10 are typically used for binding together a pair of biological tissues. In the embodiment shown throughout the Figures, the binding components 10 are shown being used for their preferred application, namely for binding together a pair of sternal halves 12 and 14 of a patient's sternum following a median sternotomy. It should, however, be understood that the binding components 10 could be used in other contexts and/or for binding together other types of biological tissues without departing from the scope of the present invention.

In the embodiment shown in FIG. 1, six binding components 10 are positioned at spaced intervals along the sternum. Typically, in the upper portion of the closure, where the manubrium portion of the sternal bone is relatively wide, the binding components 10 are inserted through the bone. Below the manubrium, the binding components 10 are usually passed through peristernal tissue between the ribs and typically do not penetrate the sternal bone except when the sternum is exceptionally wide. It should, however, be understood that any suitable number of binding components 10 could be used and that the latter could be used in any suitable combination of peristernal and/or trans-sternal approach without departing from the scope of the present invention.

Also, in FIG. 1, the loops formed by the binding components 10 are shown attached by clips C. It should be understood that the clips C are shown only by way of illustrative example and that other types of loop attachment means could be used without departing from the scope of the present invention.

Furthermore, it is contemplated within the scope of the present invention to provide clips or other suitable binding component attachment means in combination with a gauge or sensing means for gauging or sensing the axial tension in the binding component. The gauge or sensing means is preferably provided with an indicating means for providing the surgeon with an indication of the axial tension in the binding component 10. The indication could take the form of a substantially continuous read-out of the actual tension in the binding component 10 or, alternatively, could take the form of a warning signal indicating that the tension in the binding component as reached a predetermined threshold. Also, the indication can be provided in any sensorial modality including a visual signal, an audio signal, a tactile signal or a combination thereof.

In an alternative embodiment of the invention, the clip or other suitable binding component attachment means includes a means for limiting the axial tension in the binding component 10.

Figure 3:
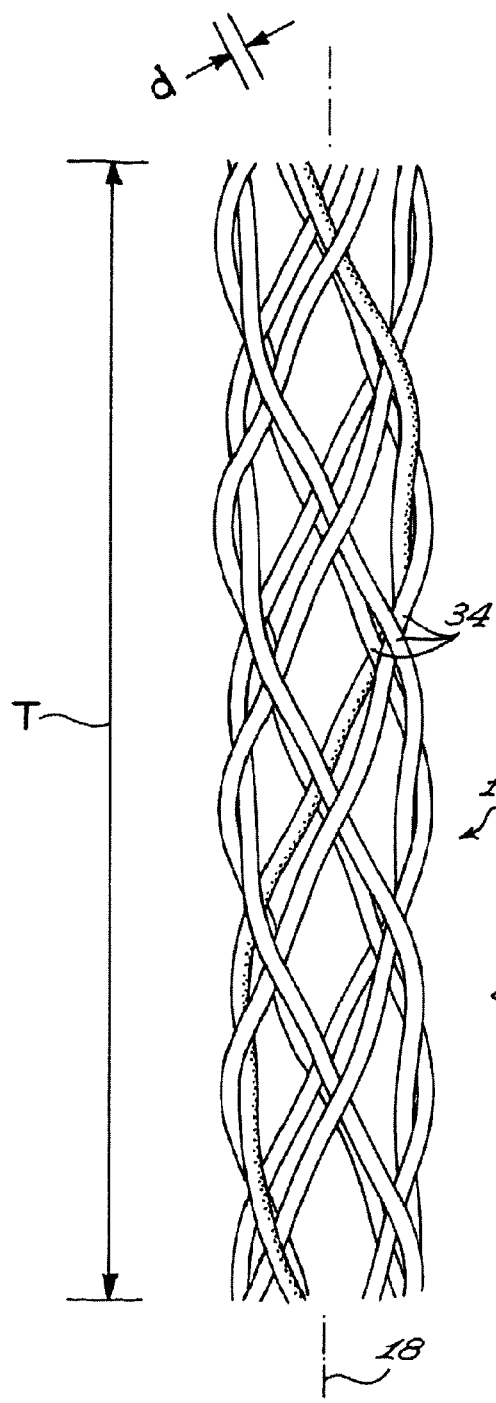
FIG. 3, in an elevational view, illustrates a binding component in accordance with an embodiment of the present invention, the binding component being shown in a substantially rectilinear configuration and in an uncompressed state.

As illustrated more specifically in FIG. 3, each binding component 10 has an elongated body 16 defining a body longitudinal axis 18. The body 16 is made, at least in part, of a shape memory material. In a preferred embodiment of the invention, the body 16 is exclusively made out of shape memory material. However, in alternative embodiments of the invention (not shown) the body 16 could be a composite construction using both a shape memory material and one or more other type of material to combine the advantageous characteristics of shape memory materials with that of the other materials.

The body 16 is configured and sized so as to be both substantially flexible and substantially compressible in a compressing direction substantially perpendicular to the longitudinal axis 18. When a body 16 having a substantially circular outer surface is used the compressing direction is inwardly radial. A radial compressive force is schematically indicated by arrow 20 in FIG. 5.

Preferably, the body 16 is configured so as to define a substantially uniform moment of inertia of bending in all directions. In an alternative embodiment of the invention (not shown), the body 16 could be configured to define at least one major moment of inertia and at least one minor moment of inertia so as to create at least one preferred bending direction.

When used in the context of suturing and, in particular, of suturing or binding together sternal halves, the body 16 preferably has a substantially uniform moment of inertia of bending in all directions so as to facilitate ergonomical manipulation during the various steps leading to sternal closure. In the context of use as sutures and, in particular, sutures for sternal halves, the body 16 is preferably provided with a relatively low moment of inertia of bending. This relatively low moment of inertia of bending is adapted to facilitate manipulation of the binding component 10 and to increase the fit between the binding component 10 and body parts when in contact with each other.

Figure 4:
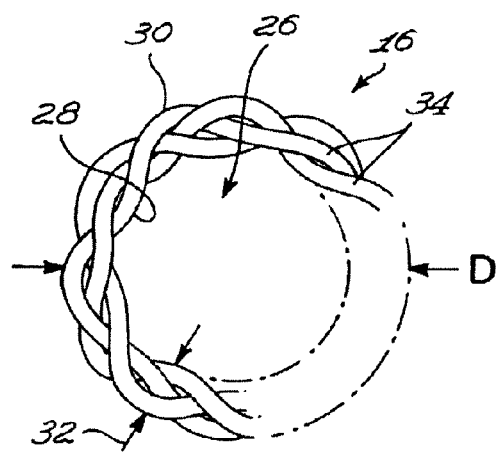
FIG. 4, in a top view, illustrates the binding component shown in FIG. 3.

In order to provide a relatively low moment of inertia of bending that is relatively uniform in all directions, the body 16 preferably has a substantially hollow tubular configuration. As shown in FIG. 4, the body 16 preferably has a substantially annular cross-sectional configuration when radially uncompressed.

Figure 2:
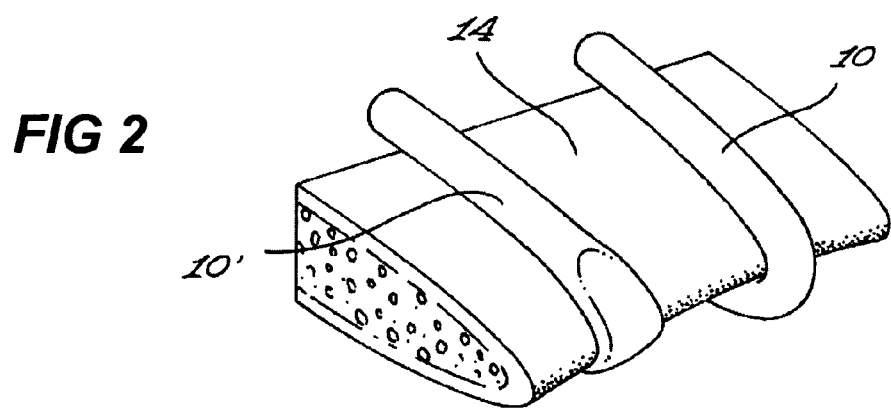
FIG. 2, in a partial perspective view with sections taken out, illustrates a pair of binding components partially wrapped around a section of a sternum, one of the binding components is radially uncompressable while the other binding component is in a radically compressed configuration.

FIG. 2 illustrates, on the right-hand side thereof, a segment of an uncompressed binding component partially wrapped around a sternum half 14. The segment on the right-hand side is schematically representative of an axially tensioned steel wire or of a non-axially tensioned binding component 10. The left-hand side of FIG. 2 illustrates a binding component 10' tensioned around the sternal half 14. As expected, the axial tension in the binding component 10' creates a radial compression adjacent the point of contact with the sternal half 14. As illustrated, the body 16 responds to the compressive pressure generated by the contact with the sternal half 14 by substantially flattening relative to its uncompressed configuration.

The propensity of the body 16 to substantially flatten upon application thereon of a radial compressive force inherently increases the size of the contact area between the body 16 and corresponding contacting portions of the sternal bone. This, in turn, inherently reduces the strain exerted locally on the sternum for a given axial load in the body 16. In other words, the radial compressibility of the body 16 helps cushion, distribute and reduce the stresses that are inflicted on the sternal bones by the binding component 10.

Figure 5:
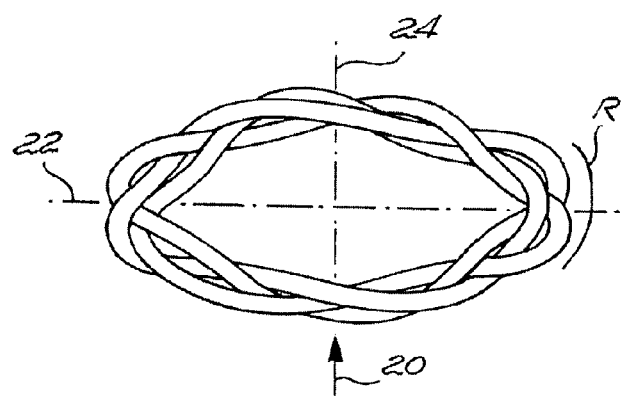
FIG. 5, in a top view, illustrates the binding component shown in FIGS. 3 and 4 in a radially compressed configuration.
Figure 6A:
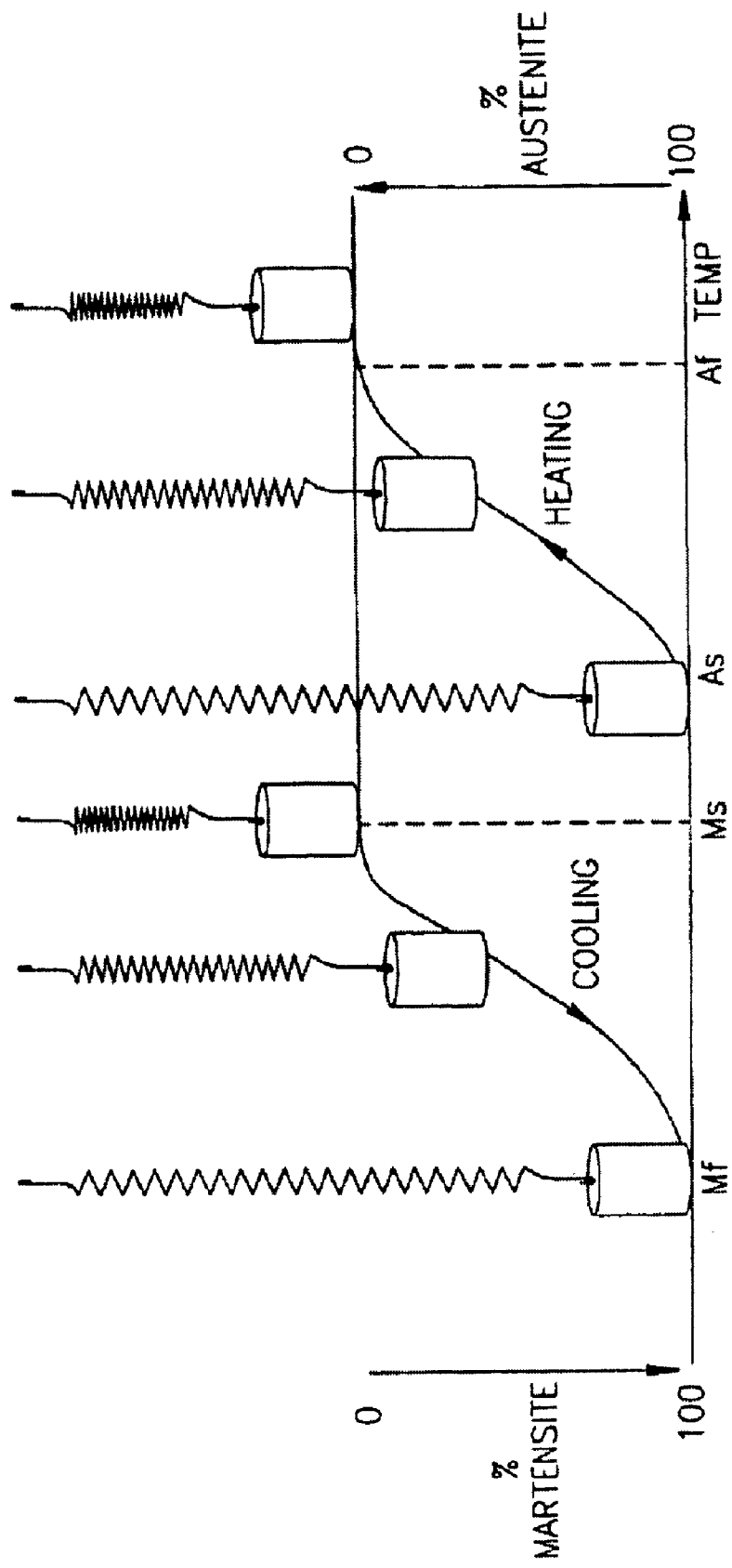
Figure 6D:
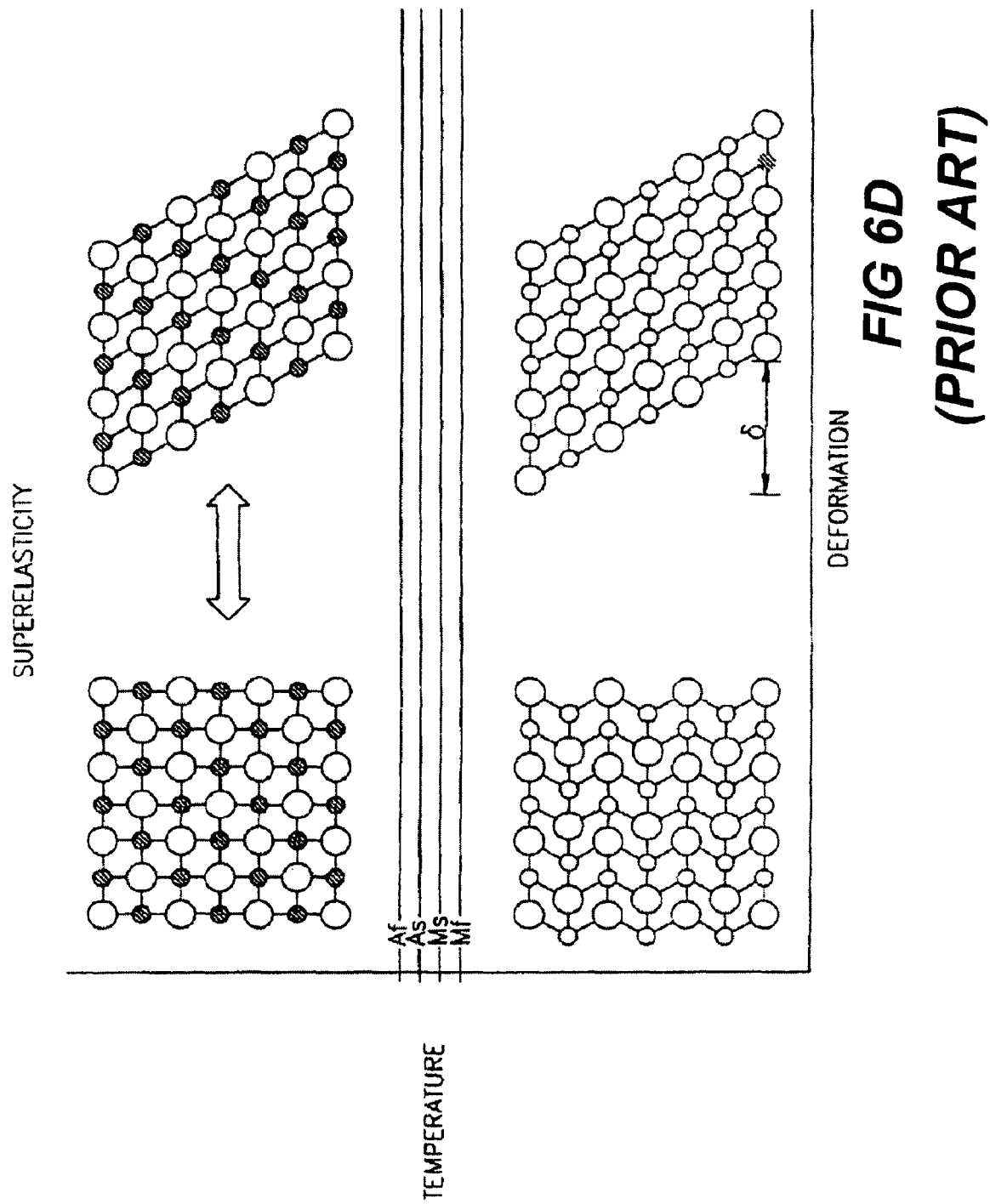
FIG. 6D schematically illustrates a typical cyclic transformation of a typical shape memory alloy, between an austenitic phase and a stress-induced martensitic phase, in accordance with the prior art.

As illustrated more specifically in FIG. 5, in a preferred embodiment of the invention, the body 16 has a substantially ovaloid cross-section when in a radially compressed configuration. The ovaloid configuration defines an oval long axis 22 and an oval short axis 24. The ratio between the oval long and short axes 22, 24 is typically approximately between 1 and 3 when substantially fittingly bent around a sternum, such as shown in FIG. 2. It should however be understood that the ratio between the long and short axes 22, 24 could have other values without departing from the scope of the present invention.

It should, however, be understood that the body 16 could assume other cross-sectional configurations when in a radially compressed configuration without departing from the scope of the present invention. However, the body 16 is preferably configured and sized so as to prevent the formation of thin or squared edges or thin-diameter cross-sections when in a radially compressed configuration so as to reduce the risks of injuring the bone or adjacent tissue surfaces.

The inherent so-called "shape memory" and "superelasticity" associated with shape memory materials are adapted to combine synergistically with the geometrical characteristics of the body 16 to evenly distribute stresses on the bone and minimize the risks of creating potentially sharp edges. Indeed, despite various potential axial loading patterns, the use of shape memory materials ensures that the advantages associated with the preferred body configuration will be retained as the shape memory materials ensure the integrity of the configuration and its compressible characteristics. More specifically, the body 16 is designed so as to demonstrate superelastic properties when subjected to temperatures substantially in the range of expected human body temperatures. Hence, when the body 16 is laterally compressed against a sternal section, it has a tendency to resiliently bias its configuration towards its initial uncompressed configuration.

This, in turn, prevents the formation of relatively sharp edges and substantially reduces the risks of kinking or other deteriorative effects.

The reference letter R is used in FIG. 5 to designate the radius of curvature of the binding component 10 adjacent the longitudinal ends of the oval long axis 22 when the binding component 10 is radially compressed by a radial compressive force 20 of a magnitude within the range used for binding together sternal halves. Typically, although by no means exclusively, the radial compressibility and the superelastic properties of the biding component 10 are balanced so that the radius of curvature R varies between (Dext-Dint)/4 and (Dext-Dint)/2 wherein Dext et Dint are respectively a body outer diameter of the body 16 and a body inner diameter of the body 16 when the binding component is radially compressed by a radial compressive force 20 of a magnitude within the range used for binding together sternal halves.

Referring back to FIG. 4, there is shown that the body 16 defines a lumen 26 extending longitudinally therethrough. The body 16 also defines a body inner surface 28 in contact with the lumen 26 and a radially opposed body outer surface 30. Typically, the body 16 defines a body thickness 32 extending radially between the body inner and outer surfaces 28, 30. The body thickness 32 typically has a value of approximately between 0.1 and 0.3 mm. It should however be understood that the body thickness 32 could have a different value without departing from the scope of the present invention.

For this range of body thickness, the radius of curvature R varies between about 0.05 mm and about 0.3 mm when the binding component is radially compressed by a radial compressive force 20 of a magnitude within the range used for binding together sternal halves.

In alternative embodiments of the invention (not shown), the lumen 16 could be filled with a different type of material or with the same material at various densities. In other words, the body 16 could define a full cross-section and be composed of a central core surrounded by a compressible peripheral sleeve.

The overall size of the body 16 can vary from between 2 mm and 5 mm. It should however be understood that the overall size of the body 16 could vary outside that range without departing from the scope of the present invention.

Preferably, the body 16 is made of braided filaments 34 of a shape memory material. Preferably, the shape memory material is a shape memory alloy. Preferably, the shape memory alloy is the biocompatible nickel and titanium alloyed commercially referred to under the acronym NITINOL (for Nickel Titanium Naval Ordnance Laboratory). NITINOL belongs to a family of intermetallic materials that contain a merely equal mixture of nickel (55 wt %) and titanium. Titanium-nickel, shape-memory alloys are biocompatible and resistant to corrosion, therefore, they are suitable for medical applications.

Alternatively the shape memory material may be selected from another suitable biocompatible shape memory alloy, a suitable biocompatible shape memory polymer or a combination thereof.

Typically, the overall denier or weight of the filaments 34 has a value of approximately 5000. It should however be understood that the overall denier could have another value without departing from the scope of the present invention. Typically, each filament 34 has a substantially disc-shaped cross-sectional configuration. Alternatively, at least some of the filaments 34 could have another cross-sectional configuration.

When the filaments 34 have a substantially disc-shaped configuration, they individually define a filament external diameter represented by the letter "d" in FIG. 3. Typically, the filament external diameter has a value substantially in the range of between 50 and 200 micrometers and preferably of about 100 micrometers. It should however be understood that the filament external diameter cold have another suitable value without departing from the scope of the present invention. Also, alternatively, the body 16 could be made up of filaments having different diameters without departing from the scope of the present invention.

Preferably, the body 16 is made of a braided structure including between 16 and 72 filaments 34. More specifically, the body 16 is preferably made up of a braided structure including approximately 24 braided filaments 34. It should however be understood that the braided structure could include any suitable number of filaments without departing from the scope of the present invention.

The thread of the filaments 34, as herein used throughout the text, refers to the distance projected on the longitudinal axis 18 by a given filament 34 as the latter completes a full turn around the longitudinal axis 18. A full thread is schematically illustrated and indicated by the letter "T" in FIG. 3. Preferably, the thread of the braided filaments 34 varies between 5 mm and 30 mm. More specifically, the thread of the braided filaments is preferably approximately 12.7 mm. It should however be understood that the thread of the braided filaments 34 could have another value without departing from the scope of the present invention.

In one embodiment of the invention, the filaments 34 are braided on conventional braider-carriers which travel around the perimeter of a braider deck to result in a tubular body 16 with the filaments 34 crossing over each other on the surface of the body 16 in a so-called criss-cross pattern. It should, however, be understood that other filament patterns such as a spiroid pattern or the like could be used without departing from the scope of the present invention.

It is within the scope of the invention to impregnate the body 16 with or otherwise apply thereto one or more medical surgically useful substances, for example, a substance which accelerates or beneficially modifies the healing process when the suture is applied to a wound or surgical site. The therapeutic agent can be chosen for its osteogenic promoting capability, its capability for promoting wound repair and/or tissue growth, its anti-microbial properties or for any other suitable indication. Anti-microbial agents such as broad-spectrum antibiotics which are solely released into the tissue can be applied in this manner to aid in combating clinical and subclinical infections in a surgical or trauma wound site.

To promote wounds repair and/or tissue growth, one of more biologically active materials known to achieve either or both of these objectives can be applied to the body 16. In the specific context of promoting the fusion of two sternal halves, the body 16 could be designed to release to or around the sternum an osteogenic factor and/or an angiogenic factor. For example, the body 16 could diffuse or otherwise distribute factors such as HGF, VEGF, BMP, PDGF, aFGF, bFGF, TGF alpha, TGF beta, other cytokines or genes.

Furthermore, the body 16 could be designed to release the osteogenic factor and/or angiogenic factor in a controlled manner such as a slow release or according to a predetermined modulated release pattern.

Application of the compositions to the body 16 can be carried out in any number of ways. For example, the body 16 can be submerged in a composition until at least wound healing enhancing amount of the composition is retained thereby. Alternatively, these healing compositions and solutions can be applied by spraying, brushing, wiping or the like on the surface of the body 16 such that the latter will receive and retain at least an effective amount of the composition. Yet, another procedure which can be used to apply the composition involves inserting the body 16 in a package containing an effective amount of the composition such that intimate contact between the body 16 and the composition will be achieved.

In accordance with the present invention, there is also provided a method for binding biological tissues together. The method includes:

selecting a suitable binding component comprising an elongated body defining a body longitudinal axis; the body being made, at least in part, of a shape memory material; the body being configured and sized so as to be both substantially flexible and substantially compressible in a direction substantially perpendicular to the longitudinal axis.

positioning the binding component in a binding configuration wherein the biological tissues are in an opposite contacting relationship relative to each other, and;

inducing a prestrain into at least part of the binding component.

Preferably, the prestrain is such that the corresponding applied stress has a value of between $\sigma_{Ms}$ and $\sigma_{Mf}$. By inducing a precharge or prestrain of a magnitude between $\sigma_{Ms}$ and $\sigma_{Mf}$ appreciable deformation reserve is provided which, in turn, contributes to maintaining a relatively important residual force at the interface between the two sternum halves. In the event of a surcharge, the greater elastic rigidity of the martensite limits opening of the sternum junction. In the event of sternum deterioration, the transformation plateau offers a reserve preserving the strain in the component 10 (up to 8% with a NiTi alloy).

Hence, as expected with the use of shape memory materials, the split sternum experiences continuous, substantially constant, pressure as the components 10 attempts to contract to a shorter length along the hysteresis stress-strain curve associated with such materials. Also, as expected with such materials, not only do the components 10 advantageously apply a substantially constant compressive force across tissue boundary but they are also able to accommodate some expansion.

The components 10 protectively control the maximum force imparted thereby on tissue in intimate contact therewith. The components 10 stretch at a known or programmable force level and are then capable of returning to their pre-stretched length while generating a constant force. The ability of the components to allow a limited expansive force moderates local forces in the tissue around the binding device, decreasing the likelihood of damaging or tearing the tissue.

The use of Nitinol not only provides interesting mechanical properties but also substantially reduces the risks of creating artefacts or other types of interference during medical imaging. Indeed, Nitinol has a much lesser potential to disrupt the images generated in a computerized axial tomography or magnetic resonance imaging scan of the chest of the patient then, for example, conventional stainless steel sternal wires. The potential to disrupt medical imaging could be even further reduced, for example, in situations wherein the body 16 is made with a shape memory polymer or a composite mixture of shape memory alloy and a shape memory polymer.

Validation of the invention was performed in three steps. In accordance with the first step, a unidimensional finite element model was conceived. The model simulated the closure of a sternum by analogy with that of a bolted joint. The model demonstrated that a sternum closure system using shape memory materials provided a residual force greater or equal to that of a standard number 5 steel wire. Accordingly, following a surcharge, the force at the interface between the two sternum halves is for the most part recuperated when a sternum closing system with shape memory materials is used. Furthermore, the rigidity of the system following opening of the sternum and the exterior force which causes opening of the sternum are both comparable to that of a steel cable.

According to a second step, an empirical model was generated in order to predict the behaviour of braided NiTi alloys using braiding parameters such as the number of filaments and the thread or longitudinal advancement per turn of the braided structure. The interior diameter of the hollow tubular braided structure was defined at 3 mm. The model allows for determination of specific parameters that will be optimized for a given sternum. Although the model incorporates a margin of error substantially in the range of 30%, it nevertheless allows for some degree of parameterization.

In accordance with a third step, laboratory tests were performed using a sternum simulator in order to compare the proposed NiTi structure with a standard stainless steel cable. These tests have demonstrated that the proposed NiTi closure system retains a residual charge greater than that of steel cables, regardless of the type of positioning (peri-sternal or trans-sternal), the density of polyurethane used or the type of loading (incremental or fatigue). Details of the validation procedure along with additional details concerning the proposed binding component or closure system are provided hereinbelow.

Example 1

Figure 7:
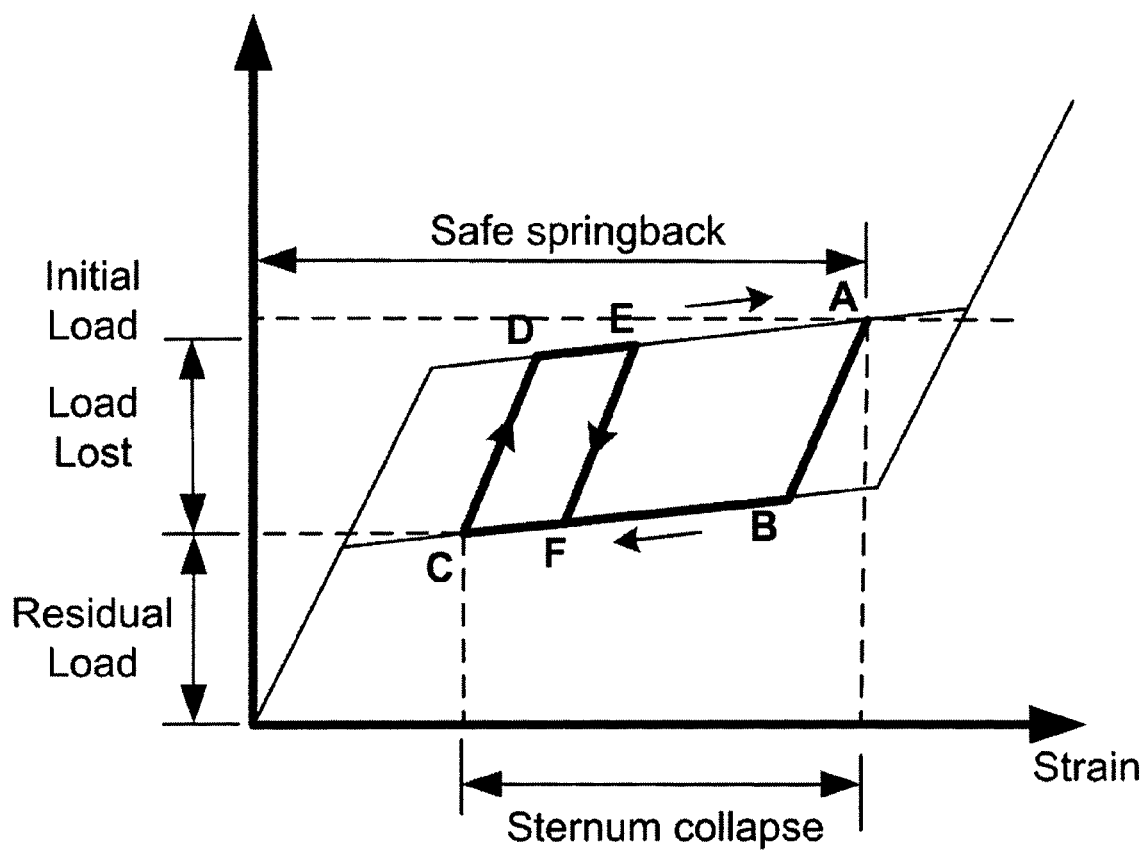
FIG. 7 schematically illustrates the principles of safe springback (segments A-B-C) and dynamic interference (segments C-D-E-F-C) of Shape Memory Alloys (SMAs) in a binding device in accordance with an embodiment of the present invention.

As seen from FIG. 7, the superelastic behaviour of the shape memory alloy (SMA) allows a non-zero zero force to be applied to the sternum even though the width of the sternum tends to decrease as a result of the nature of the healing process. This decrease in the width of the sternum is represented by portions A-B-C of the stress-strain relationship illustrated in FIG. 7. In addition, SMA benefit from the dynamic interference phenomenon [9], and manifest significant hardening under external impulses (for example coughing), as seen in the C-D portion of the stress-strain curve illustrated in FIG. 7, thus providing a quasi-constant pressure onto the sternum once a predetermined load has been reached, as seen from the D-E portion of the curve of FIG. 7. This quasi-constant pressure is defined by the height of the upper plateau of the superelastic loop. Once the disruption is over, the force applied by the closure system to the sternum returns to its initial level on the lower plateau, as illustrated in the E-F-C portion of the stress-strain curve.

Most researchers use the rigidity of a closure system as an optimization parameter: the greater the rigidity, the better the closure system. However, the rigidity of the closure system does not necessarily reflect its capacity to maintain the compression of the sternal halves either during post-operative events (for example coughing, deep breathing, sudden movement, etc.), or after the disruption is over.

In fact, it has been determined in several studies [4; 10; 11] that the sternum opens before the application of the maximum force that can be supported by the closure system, irrespective of the type of system used. A reason for this resides in the fact that the as the closure system of a given geometry becomes stiffer, a larger part of substantial stresses brought on by post-operative events such as coughing, is transferred to the sternum, and can result in its local depression, and therefore in the sternum opening under applied forces. Once the disruption is over, any permanent depression will result in a loss of compression forces at the interface between the two halves of the sternum, and consequently, in a decrease in the stability of the bond. It should be mentioned that the capacity of closure systems to reapply compression on the sternum after removing the load is not evaluated in all the aforementioned studies.

In view of the above, the following experiments have been performed. Given that compression, unlike a static fixation, is a dynamic process since it must be maintained during all dimensional redefinitions occurring in two sternum halves to be bonded, two comparison parameters for closure devices have been investigated: (1) the minimum force needed to open the bond (opening force fo), and (2) the compressive force reapplied by the closure system once the external disruption is over (residual force fr). In the context of these experiments, closure systems using braided superelastic tubes and those using conventional steel wires have been compared with the help of two complementary studies, the first being numerical and the other being experimental. A goal of the first study, which does not take into account the geometric differences between the two systems, is to evaluate the capacity of a superelastic material to accommodate a large proportion of the force exerted by the closure system on the sternum as a result of an external disruption. The second study includes the comparative experimental testing of two closure systems under two different modes of loading: single impulse (imitating coughing or sudden movement of the patient) or repeated (deep breathing).

Numerical Study

Finite elements analysis has been used to evaluate whether SMA allow the maintenance of residual forces greater than conventional materials. The influence of the geometry of the closure system has not been assessed in this portion of the study and the thoracic system (cage and sternum closure suture) has been considerably simplified. The following assumptions have been made:

1) The effect of the external disruption of the sternum is reduced by the simple forces applied at the contact points of the ribs [10].
2) Since the sternum is sufficiently long, all the wires of the closure system support an equal fraction of the force applied to the sternum [4].
3) No bond is considered to be formed between the two halves of the sternum (osteogenesis has not begun).

Description of the Model

Figure 8:
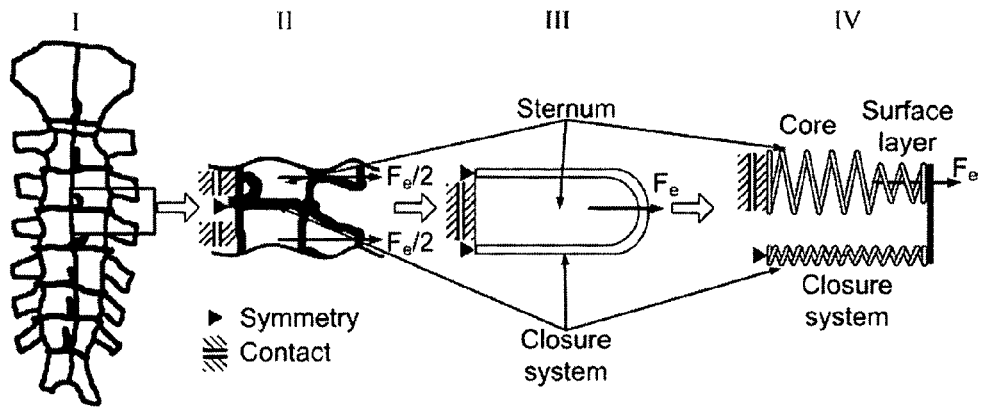
FIG. 8 schematically illustrates a simplified model a binding component in accordance with the invention: I—complete sternum (i); II—half of the sternum and of the closure system (the force created by an external disruption is transferred to the sternum through the ribs; III—cross-section of the sternum; IV—series of springs replacing the sternum and closure system.

Given its symmetric nature (force and geometry), only one half of the closure system is represented in the model, as seen in FIG. 8. The components of the closure and sternum system have been simulated by a series of springs: the closure system has been represented by a spring in tension, while the sternum has been represented by two springs in compression.

The replacement of the sternum by two springs in compression representing the core and the surface layer of the sternum models the interaction between the two halves of the sternum as well as that of the sternum with the closure system. The core spring offers resistance in compression—and not in tension—thus reflecting the absence of a bond between the two halves of the sternum. This spring represents the volume of the sternum that does not undergo any permanent deformation, but stores a part of the energy resulting form the installation of the closure system in compression. The surface layer spring accepts plastic deformations, and thus simulates the deterioration of the sternum under the action of the closure system. The external force Fe is applied at the interface between the two springs representing the sternum.

Finite Elements and Corresponding Material Laws

The finite elements model (FEM) has been built with the help of ANSYS 8.0 software by using three types of elements [12]. The SOLIDE185 finite element has been used to model both superelastic and steel closure systems: to represent the superelastic behaviour of the braided tube, the SMA material law has been applied, while the BISO material law has been used to simulate the bilinear elastoplastic behaviour of the steel wire. A 1D finite element with the BISO material law was representing the surface of the sternum with elastoplastic behaviour, while a LINK10 finite element with a Linear Elastic material law, which provides resistance in compression, but not in tension, has simulated the sternum core.

Figure 9A:
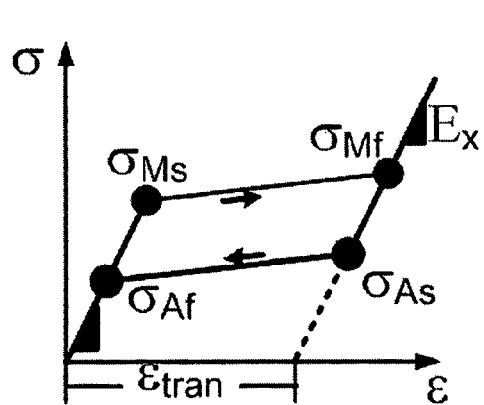
FIG. 9A, in a X-Y graph, illustrates the stress-strain curve modelling a SMA material for a Ti-50.8 at. % Ni wire with a diameter of 0.71 mm.

The SMA material law (Table 1) parameters have been obtained from tensile testing to up to 8% of strain of a Ti-50.8 at. % Ni wire with a diameter of 0.71 mm. The corresponding stress-strain curve is illustrated in FIG. 9A.

Figure 9B:
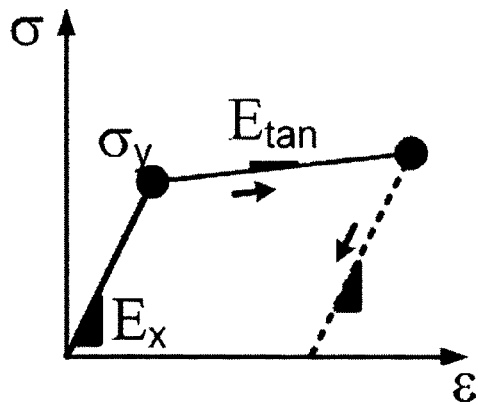
FIG. 9B, in a X-Y graph, illustrates the stress-strain curve modelling a BISO material law parameters for steel modelling a No 5 Ethicon suture wire (Somerville, N.J., USA) having a diameter of 0.78 mm.

The BISO material law parameters for steel (Table 2) has been determined from the tensile testing of a No 5 Ethicon suture wire (Somerville, N.J., USA) with a diameter of 0.78 mm. The corresponding stress-strain curve is illustrated in FIG. 9B.

The bone depression of the sternum under the cut-in action of the closing system has been modeled using data obtained with polyurethane sternum simulators (SawBones, Vashon, Wash., USA). Two densities of the sternum simulators represented two limit cases defined by Hale et al. [13]: a polyurethane with a 0.24 g/cm$^3$ density represented a "weak" sternum while a polyurethane with a 0.48 g/cm$^3$ density represented a "strong" sternum.

The material law parameters for the BISO sternum surface layer, shown in Table 3, were obtained from the indentation testing of a 0.8 mm thick steel plate into a polyurethane block that was 12.5 mm thick and 10 mm wide. The rigidity of the sternum core was set to 20 times that of the surface layer in order to avoid any significant modification of the overall sternum rigidity resulting from the surface layer depression. The half-width of the sternum was fixed at 25 mm, and the thickness of the surface layer was set at 5 mm. It was assumed that the latter completely absorbed the closure system penetration.

Calculation Algorithm

A non-limiting objective pursued with the numerical model was to compare the opening fo and residual forces fr provided by SMA and steel sternum sutures. It was assumed that the rigidity of the SMA closure system could be varied by modifying its relative stiffness between 0.05 and 0.35, while the relative stiffness of the steel wire remained constant and equal to 1 (the rigidity of the SMA braided closure system is in fact adjustable through the modification of its geometry and number of filaments [14]).

The initial force applied during the installation of the system was set at Fi=60 N for a 0.24 g/cm$^3$ sternum and at Fi=350 N, for a 0.48 g/cm$^3$ sternum since these values were close to the resistance limits for the penetration of the sternum simulators. The force resulting from external disruption varied between Fe=0 and 150 N for the low-density polyurethane and between Fe=0 and 600 N for the high-density polyurethane.

The algorithm of the numerical study could be summarized as follows (see Table 4, for numerical values):
(1) Density is selected for the sternum simulator;
(2) Material is chosen for the closure suture; if it is SMA, its relative stiffness is given an initial 0.05 value, and if it is steel, its relative stiffness is set at 1;
(3) Installation force (Fi) is applied to the closure system;
(4) External disruption is simulated by applying an initial external force Fe; if this force causes the opening of the sternum, the opening force f0 is recorded;
(5) External force is removed and residual force fr is recorded;

(6) If fr>0, the external force is incremented and steps (4)-(5) are repeated until fr=0 or maximum external force is allowed.
(7) The cross-sectional area of the SMA suture is incremented and steps (3)-(7) are repeated.

Table 4 summarizes the Finite Element Model procedure that were investigated.

Results of the Numerical Study

Figure 10:
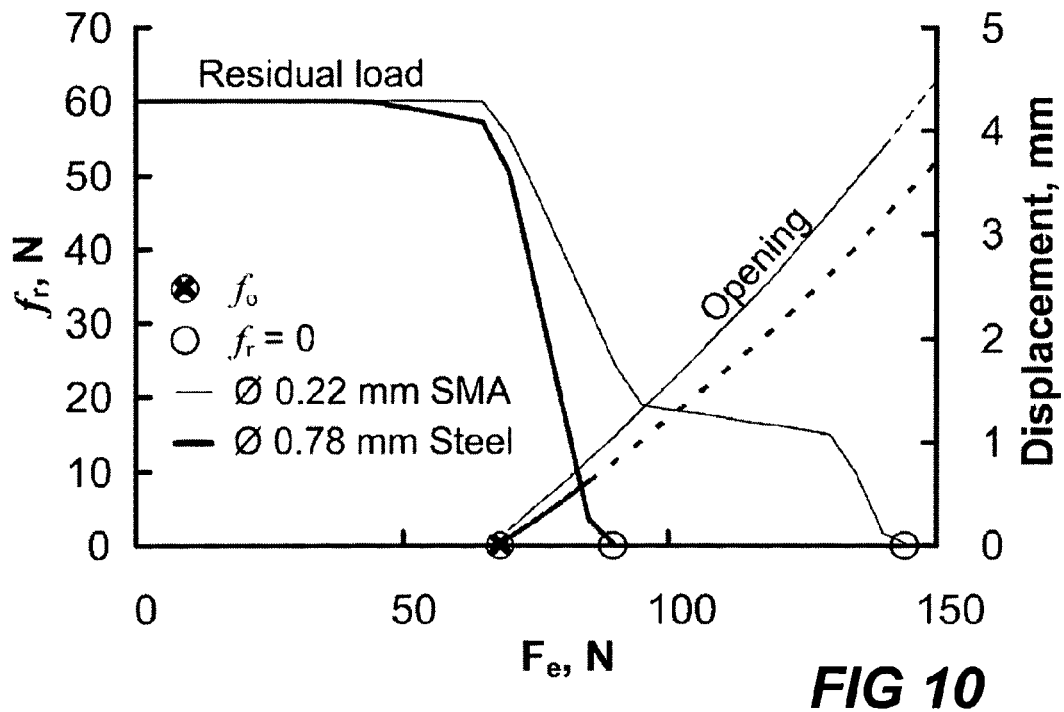
FIG. 10, in a X-Y graph, illustrates the residual force and sternum opening as a function of an external force for a 0.24 g/cm3 modelled sternum (dotted lines on the opening curves indicate that the sternum is no longer closed once the disruption is over (fr=0))

The results of the numerical study for the 0.24 g/cm$^3$ sternum are summarized in Table 5. As an example, FIG. 10 illustrates that an SMA suture with an equivalent diameter of 0.22 mm maintained a non-zero residual force at the sternum interface (fr≧0) after an external force Fe, which is 60% greater than that supported by a Ø0.78 mm steel wire: 145 N as opposed to 90 N. However, this was at the expense of a larger sternum opening: after an identical external force of 90 N, the SMA suture allowed a sternum opening of 1.1 mm, while the steel suture allowed an opening of 0.8 mm. Also, the minimum sternum opening force fo is approximately 70 N for all sternum closure devices, which is comparable to the experimentally obtained data [4].

For the 0.48 g/cm$^3$ sternum model, SMA sutures allowed a residual force to be maintained for external forces Fe greater than 600 N, which is more than twice the force of a severe coughing fit [10]). In comparison, the residual force provided by steel sutures became zero after an external force of 400 N.

Experimental Study

To consider the geometry of the SMA sternum closure system, a series of experimental tests were undertaken.

Description of the Testing Bench

Figure 11:
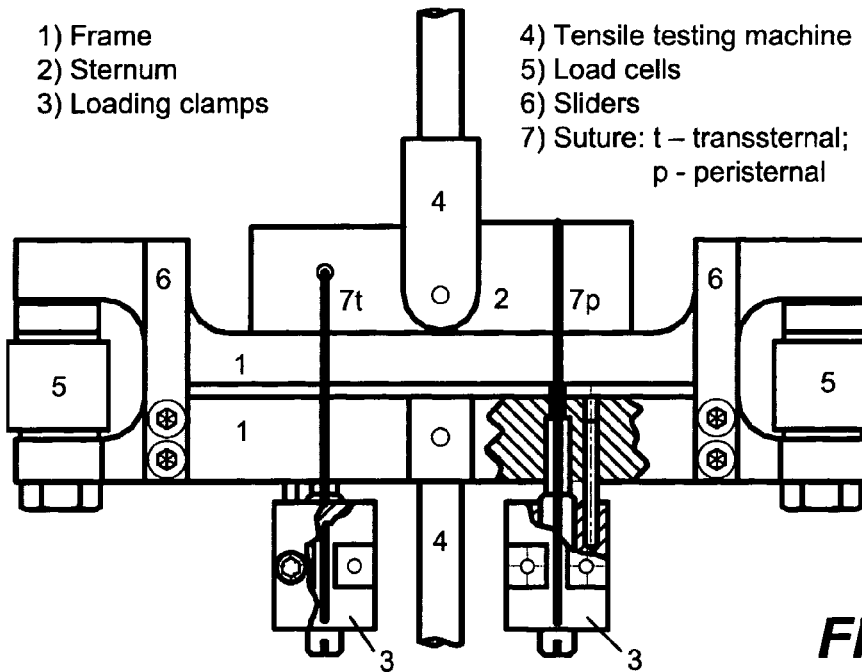
FIG. 11, in a schematic view, illustrates a testing bench used to test binding components in the form of sternum closing systems.

FIG. 11 shows the outline of the testing bench used. Two identical closure systems (7) were installed simultaneously on polyurethane blocks (2) simulating the sternum. The installation force was applied with the help of two adjustable loading clamps (3). Two LC703-100 load cells (5) (Omega, Stamford, Conn., USA) installed on each extremity of the testing frame (1) allowed the force at the sternum interface to be measured. An Enduratec ELF 3200 tensile testing machine (4) was used to apply external force. LabView 6.0 (National Instruments Corp., Austin, Tex., USA) data acquisition systems registered the real time displacement of the testing machine's piston as well as the forces measured by the load cells.

Components Used

A comparison was made between two closure devices: (1) Ø0.78 mm No 5 Ethicon steel wire and Ø3 mm SMA braided 12.5 mm pitch tube made of 24 Ø0.1 mm filaments of Ni—Ti—Cr alloy.

The 25×10×90 mm polyurethane blocks with a density of 0.24 and 0.48 g/cm$^3$ were used to simulate sternum bones. One of the sides of the samples used for a peristernal installation (FIG. 11, right) was rounded to simulate the edge of the sternum, and those used for the transsternal installation (FIG. 11, left) featured 2.4 mm diameter holes pierced 10 mm from the symmetric plane in order to allow the threading of the closure device.

Figure 12:
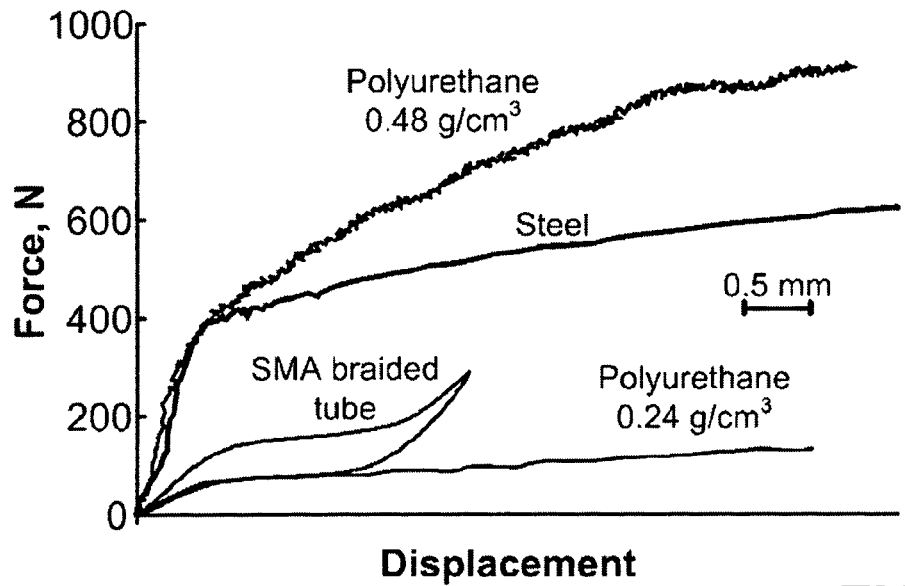
FIG. 12, in a X-Y graph, illustrates the force-displacement diagrams of some components of the testing bench of FIG. 11.

The force-displacement diagrams of the sternum simulators (indentation testing) and of the two types of sternum sutures (tensile testing) are shown in FIG. 12.

Experimental Procedure

Testing Modalities

The experiment was planned to allow two closure systems to be compared under different exploitation conditions: severe coughing (single impulse loading) or deep breathing (cyclical loading), in the case of peristernal or transsternal installations, and for two sternum densities (0.24 and 0.48 g/cm$^3$)—as seen in Table 6.

The Following Two-Step Procedure was Performed:
1. Application of the Installation (Initial) Force Fi The initial force Fi applied to the median sternum closure was a function of the density of the polyurethane sternum simulator. The higher the density, the higher the initial force that can be applied. The initial force for the 0.24 g/cm$^3$ sternum was set at the same level as for the numerical study: 60 N (see Table 4). For the 0.48 g/cm$^3$ sternum, it was set at 200 N.
2. Application of the External Force Fe The Single impulse loading mode simulated coughing or sudden movement, and consisted in a series of loading-unloading cycles with incrementally increased amplitude. Each cycle took 10 seconds, and a 15-second dwell time at zero force was respected prior to each subsequent cycle. At each cycle, the force was increased by 25 N, up to a maximum value allowed, which was 125 N for the 0.24 g/cm$^3$ sternum and 445 N for the 0.48 g/cm$^3$ sternum (the latter value was limited by the capabilities of the testing machine). The measurement of the residual force fr was performed prior to each force increment.

Cyclic loading simulated deep breathing and consisted in 500 cycles of a sinusoidal force varied with a 0.5 Hz frequency between 0 and 60 N (0.24 g/cm$^3$ sternum) and 0 and 200 N (0.48 g/cm$^3$ sternum). The measurement of the residual force was completed after the 500th cycle at zero load.

Results

Figure 13:
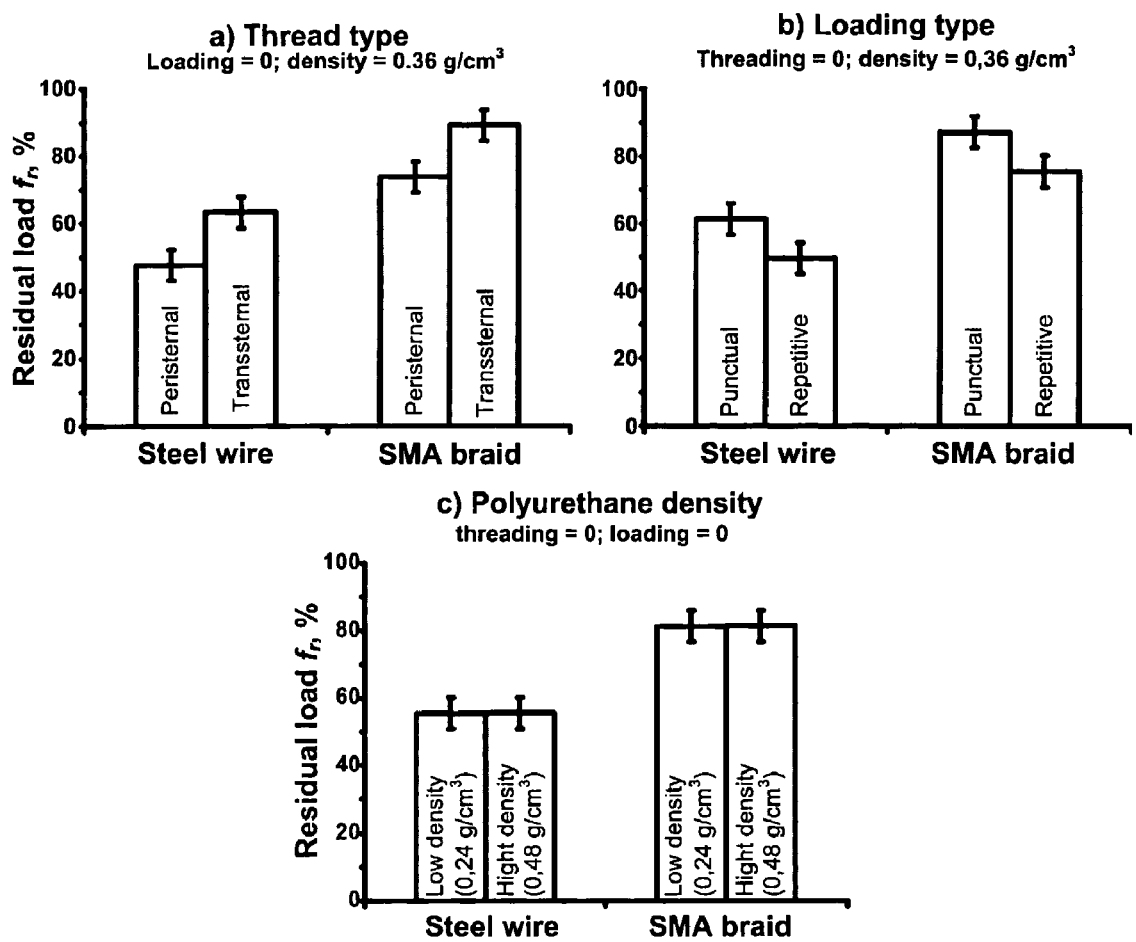
FIG. 13, in bar graphs, illustrates the relative residual force R=fr/Fi provided by two binding devices in the form of experimental closure systems as a function of thread type installation mode (peristernal versus transsternal) (panel a); as a function of a loading mode (single impulse versus repetitive loading) (panel b); and foam used to test the closure systems (panel c)

The StatGraphics software (StatPoint Inc., Herndon, Va.) was used to analyse the results obtained [15]. The outcome variable was the relative residual force R=fr/Fi. FIG. 13 demonstrates that the use of the SMA suture compared to steel suture allows an average gain of 30% in the relative residual force value as compared to using a steel suture. The results for the other statistically significant (p≦0.05) input variables show that the peristernal installation guarantees higher residual forces than the transsternal installation, and that a large single impulse force causes more damage than light repetitive forces. The effect of the sternum model density variation was not significant.

Discussion

The experimental study allows the combined effect of the superelastic behaviour and of the tubular geometry of the SMA to be taken into account. In the context of this study, a unique 24-filament SMA braided tube with an inside diameter of 3 mm was tested with sternum simulators having two limit densities.

For the 0.24 g/cm$^3$ sternum, the 24-filament SMA suture was a bit too rigid. It is therefore likely that the increased contact area between the sternum and closure system was mostly responsible for the 30% gain in residual force when compared to a steel suture. For the 0.48 g/cm$^3$ sternum, the 24-filament SMA suture was a bit too compliant. Nevertheless, the advantage of using a superelastic suture led to a similar 30% gain in residual force as compared to a steel suture. In fact, the 24-filament SMA suture would have demonstrated maximum efficiency for an intermediate density 0.32 g/cm$^3$.

To reduce the risk of sternum breakage, a median sternotomy closure using a superelastic tubular braid was proposed. The numerical model allowed the net benefit of a binding component in the form of an SMA suture to be demonstrated against the performance of a No 5 Ethicon steel suture. It was experimentally proven that the SMA suture preserved compression at the sternum interface when an external disruption occurs, at forces 30 to 60% greater than those endured by the No 5 Ethicon suture regardless of the installation technique used (peristernal or trans-sternal), the type of external force applied (single impulse or repetitive), and the sternum density.

The above suggests a method for selecting a force-displacement characteristic of a binding component and for manufacturing and using the same. This method is illustrated with the help FIG. 14, which shows an example of a suitable stress-strain curve usable for determining parameters of the binding component. The reader skilled in the art will readily appreciate that while the present document illustrates by way of example a method for manufacturing and using a binding component for closing a sternum, similar methods are usable to manufacture devices that bind together any other suitable biological tissues.

The method includes selecting a predetermined force-displacement relationship for the structures to bind. For example, this force-displacement relationship is a force-displacement corresponding to a "cut-through" test. This force-displacement relationship may be selected from known force-displacement relationships. For example, if the biological tissues to bind are bones, the force-displacement relationship may be obtained experimentally by a cut-through testing of a bone simulator (for example solid polyurethane biomechanical test blocks) by an indenter taking the form of a wire or of a thin-plate shape. In other examples, the force-displacement curves may be modelled from the density, dimensions and types of bones to bind. The density of the bones may be estimated for a given patient through a CT bone scan or any other suitable imaging modality. In another example, a predetermined bone density is assumed.

It should be noted that it is not necessary to measure a bone density to manufacture a binding component in accordance with the claimed invention. Indeed, various binding components corresponding to various predetermined bone densities may be manufactured. Then, when the binding component is installed, a specific binding component is selected for a specific patient according to a selection criterion. An example of a selection criterion includes selecting a binding component that has been manufactured assuming that a bone density of the bones to bind is about equal to a bone density measured in the patient.

For a sternum, the bone density is such that the sternum is typically modelled using a solid rigid polyurethane foam having a density of from about 0.24 g/cm$^3$ to about 0.48 g/cm$^3$. The lower end of this range corresponds generally to the sternum of patients suffering from osteoporosis. In some embodiments of the invention, the bone density of the patient is not known. In these cases, the assumption of a low bone density, for example corresponding to a foam having a density of 0.24 g/cm$^3$, may be advantageous to reduce risks of bone fracture.

Figure 14:
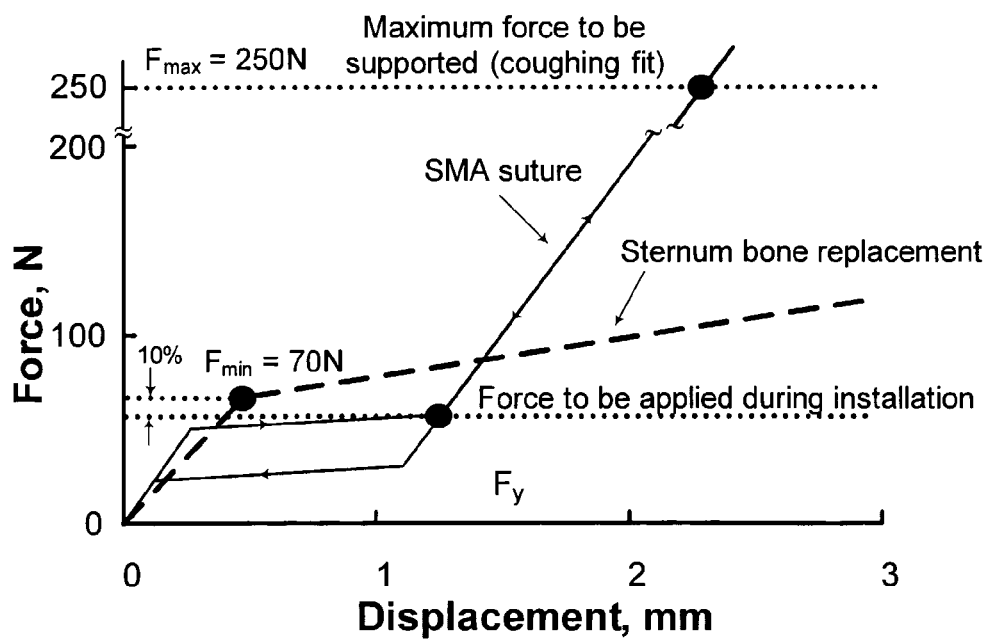
FIG. 14, in a schematic view, illustrates a selection technique for SMA suture force-displacement characteristics in accordance with an embodiment of the present invention.

The curve identified as (1) sternum in FIG. 14 illustrates an example of a model of a cut-through displacement-force relationship for a sternum. This model assumes a bilinear relationship wherein the sternum deforms linearly for small displacements. Then, after the yield limit of the sternum has been reached, the sternum deforms irreversibly and linearly with displacement with a lower resistance to deformation.

As mentioned hereinabove, the force exerted on the binding component by the biological tissues to bind typically diminishes after installation of the binding component. Therefore, to preserve compression between biological structures to bind, it is desirable to exert a relatively large force on the biological tissues when installing the binding component. To that effect, the binding component is prestrained at a level corresponding to a predetermined prestrain force. For example, the predetermined prestrain force is from about 80 to about 95% of the yield limit of a sternum. In a specific example of implementation, the predetermined prestrain force is about 90% of the yield limit of the sternum.

To improve the capability of the suture to support post-operative events, such as the patient coughing, with reduced risks of failure, the minimum suture resistance, or in other words the ultimate tensile strength, to achieve is set at a predetermined level. For example, in the case of a sternum, this predetermined level is set to between about 200N and about 300N, and more specifically to about 250 N, as determined for a severe coughing fit [10].

Parameters of the binding device that maximize the residual force fr remaining after the post-operative event is finished are determined. For example, the following variables may be varied: number of filaments, pitch, inside diameter, pitch or helix angle and materials included in the binding device, among others. More details regarding these parameters are found in reference [14]. This maximization is performed, for example, through an iterative modelling process. Methods for optimizing material properties and structures are well-known in the art and will therefore not be described in further details herein.

In some embodiments of the invention, the maximization of the residual force fr is performed assuming that the displacement-force relationship is similar to the relationship illustrated by the parallelogram-shaped hysteresis curve identified as "(4) SMA braid" in FIG. 14. As shown from this Figure, this relationship includes upper and lower substantially linear plateaus substantially parallel to each other that are connected through straight line segments at both ends thereof. In a specific example of implementation, the residual force fr is maximized by selecting the material composition, dimensions, configuration of the binding component or of its body so that the difference in force between the lower plateau of the force-displacement relationship of the binding component and the upper plateau of the force-displacement relationship of the binding component is minimal.

The maximization of fr may be performed while satisfying the following criterion: the knee point, or inflection point, between the upper plateau of the SMA curve and the elastic slope of a stress-induced martensite phase should be substantially coincident with the point representing the pretension in the binding device during installation.

All the constraints described hereinabove have, when simultaneously satisfied, a synergetic effect and provide binding components that have unexpected characteristics. However, in some embodiments of the invention, only some of these constraints are satisfied in specific binding components.

A specific example of a binding component that has been found to be suitable to bind two halves of a sternum includes 24 filaments of a Ni—Ti—Cr alloy wire having a diameter of 0.075 mm. The wires are braided with a pitch of about 12.5 mm to produce a substantially tubular structure having a diameter of about 3 mm. While parameters describing this binding component have been found using the above-described method, the reader skilled in the art will readily appreciate that this method should not be used to limit the scope of the claimed invention in apparatus claims.

The above-described example also suggests that a difference in force between the lower plateau of the force-displacement relationship of a binding component in accordance with the invention and the upper plateau of the force-displacement relationship of this binding component of from about 10 percent to about 30 percent of the force to which the prestrain corresponds is achievable.

From the results relating to the 0.24 g/cm³ foam, which models a typical osteoporotic sternum, a suitable value of a prestrain to which the body of the binding component imay be prestrained is a prestrain corresponding to that generated by a force having a magnitude of from about 55-65 N, or of about 60 N. The use of this prestrain is advantageous in binding component for binding osteoporotic sternums as it helps in minimizing the risks of fractures of the sternum by the binding component.

Although the present invention has been described hereinabove by way of preferred embodiments thereof, it can be modified without departing from the spirit, scope and nature of the subject invention, as defined in the appended claims.

TABLE 1

SMA (ANSYS) material law used to model a superelastic binding component

| Param. | Unit | Value |
|---|---|---|
| Ex | MPa | 32000 |
| etrans | m/m | 0.037 |
| σMs | MPa | 335 |
| σMf | MPa | 385 |
| σAs | MPa | 200 |
| σAf | MPa | 150 |

TABLE 2

BISO (ANSYS) material law used to model a N°5 Ethicon steel binding component

| Param. | Unit | Value |
|---|---|---|
| Ex | MPa | 90000 |
| Etan | MPa | 425 |
| σy | MPa | 1600 |

TABLE 3

BISO material law for the surface layer and Linear Elastic material law (ANSYS), for a modelled sternum core.

| | | Surface layer | | Core | |
|---|---|---|---|---|---|
| Mat law | | BISO | | Linear Elastic | |
| Param. | Unit | 0.24* | 0.48* | 0.24* | 0.48* |
| Ex | MPa | 735 | 5200 | 14 700 | 104 000 |
| $E_{tan}$ | MPa | 140 | 1050 | | |
| $\sigma_y$ | MPa | 67 | 400 | | |

*Polyurethane density (g/cm3)

TABLE 4

Sequence of FEM procedures followed in numerical modelling of a binding component in accordance with an embodiment of the present invention.

| Suture | Materials | | Suture relative stiffness; increment | External force $F_e$ range; increment (N) |
|---|---|---|---|---|
| | Sternum density (g/cm³) | $F_i$ (N) | | |
| Steel | 0.24 | 60 | 1 | [0-150]; 5 |
| | 0.48 | 350 | | [0-600]; 20 |
| SMA | 0.24 | 60 | [0.05-0.35]; 0.05 | [0-150]; 5 |
| | 0.48 | 350 | [0.5-1.3]; 0.1 | [0-600]; 20 |

TABLE 5

Results of a numerical model modelling the interaction of a binding device with a foam model of a sternum having a density of 0.24 g/cm³.

| Wire type | Suture relative stiffness | Equivalent diameter (mm) | External force $F_e$ corresponding to $f_r = 0$ (N) |
|---|---|---|---|
| SMA | 0.05 | 0.16 | 100 (wire break) |
| | 0.10 | 0.22 | 145 |
| | 0.15 | 0.27 | 135 |
| | 0.20 | 0.32 | 95 |
| Steel (n°5) | 1.00 | 0.78 | 90 |

TABLE 6

Experimental testing modalities for a closure system.

| Variable | Modalities | |
|---|---|---|
| Closure system | Steel suture | SMA suture |
| Polyurethane density | 0.24 g/cm³ | 0.48 g/cm³ |
| Threading | Transsternal | Peristernal |
| Loading | Single impulse | Cyclic |

REFERENCES

[1] Heart disease and stroke statistics—2005 Update. (2005). Dallas: American Heart Association.

[2] Milton, H. (1987). Mediastinal surgery. Lancet, 1, 872-875.

[3] Robicsek, F., Daugherty, H. K., & Cook, J. W. (1977). The prevention and treatment of sternum separation following open-heart surgery. The Journal of Thoracic and Cardiovascular Surgery, 73(2), 267-268.

[4] Casha, A. R., Gauci, M., Yang, L., Saleh, M., Kay, P. H., & Cooper, G. J. (2001). Fatigue testing median sternotomy closures. European Journal of Cardio-thoracic Surgery, 19(3), 249-253.

[5] Soroff, H. S., Hartman, A. R., Pak, E., Sasvary, D. H., & Pollak, S. B. (1996). Improved sternal closure using steel bands: Early experience with three-year follow-up. Annals of Thoracic Surgery, 61(4), 1172-1176.

[6] Combes, J. M., Carrie, J. M., Soula, P., Tricoire, J. L., & Cerene, A. (1993). Fermeture des sternotomies à l'aide des agrafes de Cotrel. Annales De Chirurgie, 47(2), 179-183.

[7] Sargent, L. A., Seyfer, A. E., Hollinger, J., Hinson, R. M., & Graeber, G. M. (1991). The healing sternum: a comparison of osseous healing with wire versus rigid fixation. The Annals of Thoracic Surgery, 52(3), 490-494.

[8] Losanoff, J. E., Richman, B. W., & Jones, J. W. (2002). Disruption and infection of median sternotomy: a comprehensive review. European Journal of Cardio-Thoracic Surgery, 21(5), 831-839.

[9] Duerig, T., Pelton, A., & Stockel, D. (1997, March). Superelasitic Nitinol for Medical Devices. Medical Plastics and Biomaterial Magazine MPV archive.

[10] Casha, A. R., Yang, L., Kay, P. H., Saleh, M., & Cooper, G. J. (1999). A biomechanical study of median sternotomy closure techniques. European Journal of Cardio-Thoracic Surgery, 15(3), 365-369.

[11] McGregor, W. E., Trumble, D. R., & Magovern, J. A. (1999). Mechanical analysis of midline sternotomy wound closure. The Journal of Thoracic and Cardiovascular Surgery, 117(6), 1144-1145.

[12] ANSYS. (2003). ANSYS (Version 8.0) [Finites elements]. Canonsburg, Pa., US.

[13] Hale, J. E., Anderson, D. D., & Johnson, G. A. (1999, Oct. 21-23). A polyurethane foam model for characterizing suture pull-through properties in bone. Paper presented at the 23rd Annual Meeting of the American Society of Biomechanics, University of Pittsburgh.

[14] Baril, Y. (2004). Design and Modelisation of a Sternum Closure System (in French). Master Thesis, École de technologie supérieure, Montreal.

[15] Montgomery, D. C. (1996). Design and analysis of experiments (4th edition ed.). New York.

We claim:

1. A method for binding biological tissues together, the biological tissues having a tissue temperature, the biological tissues also having a yield limit beyond which the biological tissues are irreversibly deformed, said method comprising:

selecting a suitable binding component comprising an elongated body defining a body longitudinal axis, said body being made, at least in part, of a shape memory material;

positioning said binding component in a binding configuration wherein said binding component biases said biological tissues in an opposite contacting relationship relative to each other; and after said positioning of said binding component, applying to said binding component a prestrain causing the generation of a prestrain force within an interval of from about 80 percent to about 95 percent of a yield force, said yield force corresponding to the yield limit of the biological tissues, said prestrain force also corresponding to a prestrain stress in said binding component, said prestrain stress having a magnitude between $\sigma_{Ms}$ and $\sigma_{Mf}$ at said tissue temperature;

wherein said body has a composition, a configuration and dimensions such that an inflection point between an upper plateau of a force-displacement relationship of said binding component and a linear force-displacement relationship representing an elastic deformation of a stress-induced martensite phase in said binding component is coincident with said prestrain force and a displacement in said binding component corresponding to said prestrain.

2. A method as defined in claim 1, wherein said prestrain force is about 90 percent of the yield force corresponding to the yield limit after said positioning of said binding component.

3. A method as defined in claim 1, wherein the biological tissues are bones and the binding component has a binding component ultimate tensile strength, said binding component ultimate tensile strength being reached when a force within the interval of from about 200 N to about 300 N is applied to the binding component.

4. A method as defined in claim 3, wherein said binding component ultimate tensile strength is reached when a force of about 250 N is applied to the binding component.

5. A method as defined in claim 1, wherein said body is configured and sized so as to be both substantially flexible and substantially compressible in a direction substantially perpendicular to said longitudinal axis.

6. A method as defined in claim 1, wherein the biological tissues are bones, said method further comprising measuring the density of the bones and determining the yield limit of the bones using at least in part the measured density of the bones.

* * * * *